(12) United States Patent
Aoki et al.

(10) Patent No.: US 6,288,236 B1
(45) Date of Patent: Sep. 11, 2001

(54) BENZIMIDAZOLE COMPOUNDS CONTAINING A BENZOXAZOLE OR BENZOTHIAZOLE RING, AND COMPOSITIONS AND METHODS OF USE CONTAINING THE SAME

(75) Inventors: Kozo Aoki, Kanagawa; Kazuhiro Aikawa, Kanagwa, both of (JP)

(73) Assignee: Fuji Photo Film Co., Ltd., Kanagawa (JP)

( * ) Notice: Subject to any disclaimer, the term of this patent is extended or adjusted under 35 U.S.C. 154(b) by 0 days.

(21) Appl. No.: 09/688,146

(22) Filed: Oct. 16, 2000

Related U.S. Application Data

(62) Division of application No. 09/409,685, filed on Sep. 30, 1999, now Pat. No. 6,174,907, which is a division of application No. 09/000,351, filed as application No. PCT/JP96/01949 on Jul. 12, 1996, now Pat. No. 5,998,456.

(30) Foreign Application Priority Data

Jul. 17, 1995 (JP) .................................................... 7-180167
Jul. 28, 1995 (JP) .................................................... 7-192777

(51) Int. Cl.[7] ..................... C07D 271/113; C07D 271/07
(52) U.S. Cl. ......................... 548/132; 546/269.4; 548/144
(58) Field of Search .................................... 548/132, 144; 546/269.4

(56) References Cited

U.S. PATENT DOCUMENTS

| | | | |
|---|---|---|---|
| 4,814,329 | 3/1989 | Harsanyi et al. | 514/211 |
| 4,873,346 | 10/1989 | Anderson | 548/157 |

FOREIGN PATENT DOCUMENTS

| | | |
|---|---|---|
| 632040 | 1/1995 | (DE) . |
| 0167943A2 | 1/1986 | (EP) . |
| 0352864A2 | 1/1990 | (EP) . |
| 0583665A2 | 2/1994 | (EP) . |
| 52-62275 | 5/1977 | (JP) . |
| 57-158767 | 9/1982 | (JP) . |
| 2-91040 | 3/1990 | (JP) . |
| 2-167268 | 6/1990 | (JP) . |
| 6-299374 | 10/1994 | (JP) . |
| 7-17971 | 1/1995 | (JP) . |
| WO9426738 | 11/1994 | (WO) . |
| WO9640645 | 12/1996 | (WO) . |

OTHER PUBLICATIONS

F. M. Whittington et al., "International Journal of Obesity", XP–002076231, vol. 11, No. 6, pp. 619–629, 1987.

*Primary Examiner*—Laura L. Stockton
(74) *Attorney, Agent, or Firm*—Birch, Stewart, Kolasch & Birch, LLP

(57) ABSTRACT

Benzimidazole compounds represented by the formula set out below and analogs thereof, wherein Y represents a single bond or sulfur atom; Z represents oxygen atom, sulfur atom, or N—$R^4$; $R^1$ and $R^2$ independently represent hydrogen, a halogen atom, alkyl group or other; $R^3$ and $R^4$ independently represent hydrogen, alkyl group, acyl group or other; n and m independently represent an integer of 1, 2, or 3; and L represents a linking group such as $C_{2-12}$ alkylene group or an alkylene group containing one or more phenylene groups or ether groups. The compounds are useful as an active ingredient of a medicament such as a preventive and therapeutic medicament for hyperlipemia or arterial sclerosis.

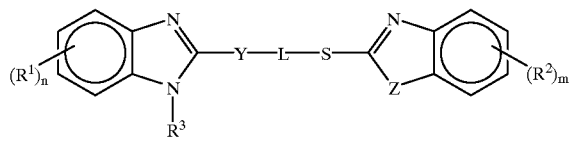

10 Claims, No Drawings

BENZIMIDAZOLE COMPOUNDS CONTAINING A BENZOXAZOLE OR BENZOTHIAZOLE RING, AND COMPOSITIONS AND METHODS OF USE CONTAINING THE SAME

This application is a divisional application Ser. No. 09/409,685, filed on Sep. 30, 1999, now U.S. Pat. No. 6,174,907, which is a Divisional application Ser. No. of 09/000,351 filed on Jan. 16, 1998 now U.S. Pat. No. 5,998,456. application Ser. No. 09/000,351 is the national phase of PCT International Application No. PCT/JP96/01949 filed on Jul. 12, 1996 under 35 U.S.C. § 371. The entire contents of each of the above-identified applications are hereby incorporated by reference.

TECHNICAL FIELD

The present invention relates to benzimidazole compounds. More precisely, the present invention relates to novel bis-type benzimidazole compounds which are useful as an active ingredient of a medicament for therapeutic and preventive treatment of hyperlipemia, arterial sclerosis and the like, or useful as an additive of a silver halide photosensitive material, a liquid crystal material and the like.

BACKGROUND ART

In recent years, patients with so-called adult diseases such as arterial sclerosis, hypertension, and diabetes mellitus have been continuously increasing with prolongation of life expectancy. In particular, patients with hyperlipemia and arterial sclerosis derived therefrom have been remarkably increasing due to excessive intake of high calorie and high cholesterol food, which have become a serious social problem. Medicaments currently used for drug therapy of hyperlipemia and arterial sclerosis are those symptomatically lower cholesterol in blood, and therefore, they cannot be expected to have potency in retracting arterial sclerosis lesions, per se. Arterial sclerosis is characterized by lesions of intimal hyperplasia and lipid accumulation in blood vessels, and it has been elucidated from recent biochemical findings that foaming of macrophages plays a main role in the formation of arterial sclerosis lesions. Accordingly, suppression of the foaming of macrophages may possibly prevent arterial sclerosis by inhibiting formation of arterial sclerosis lesions, or achieve radicular treatment of arterial sclerosis by retraction of arterial sclerosis lesions. However, no medicament having such activity has been known.

Therefore, an object of the present invention is to provide a compound having activity of suppressing the foaming of macrophages, and is useful as an active ingredient of a medicament for preventive and/or therapeutic treatment of arterial sclerosis. Another object of the present invention is to provide a compound having the aforementioned activity, and is useful as an active ingredient of medicament for preventive and/or therapeutic treatment of hyperlipemia.

DISCLOSURE OF THE INVENTION

The inventors of the present invention conducted various research to achieve the foregoing objects, and as a result, they found that novel benzimidazole compounds represented by the formulas set out below have activity of suppressing the foaming of macrophages, and are useful as active ingredients of preventive and therapeutic medicament of arterial sclerosis and preventive and therapeutic medicament of hyperlipemia. The present invention was achieved on the basis of this finding.

According to the first aspect of the present invention, there are provided benzimidazole compounds represented by the following formula (IA):

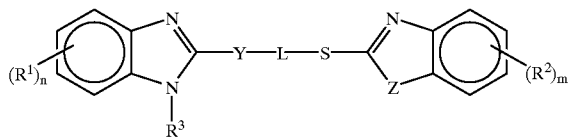

wherein, Y represents a single bond or sulfur atom; Z represents oxygen atom, sulfur atom or N—$R^4$; $R^1$ and $R^2$ independently represent hydrogen atom, a halogen atom, an alkyl group, a haloalkyl group, an aryl group, an alkoxy group, an aryloxy group, an alkoxycarbonyl group, a carbamoyl group, a sulfamoyl group, an acylamino group, a sulfonylamino group, cyano group, hydroxyl group, or nitro group; $R^3$ and $R^4$ independently represent hydrogen atom, an alkyl group, an acyl group, a sulfonyl group, an alkoxycarbonyl group, a sulfamoyl group, or a carbamoyl group; n and m each independently represent an integer of 1, 2 or 3, and where n or m represents 2 or 3, two or three $R^1$ or $R^2$ which may be the same or different substitute on the benzene ring, respectively; and L represents a linking group selected from a group consisting of a $C_{2-12}$ alkylene group, and an alkylene group containing one or more phenylene groups or ether groups and having 4–12 atoms that constitute a full length of a linking chain; provided that $R^1$ and $R^2$ do not represent the same substituents when Y is sulfur atom, Z is N—$R^4$, n=m, and $R^3$ and $R^4$ represent the same substituents.

According to the second aspect of the present invention, there are provided benzimidazole compounds represented by the following formula (IB):

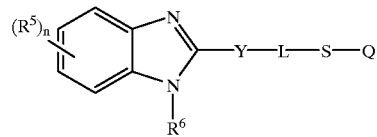

wherein, Y represents a single bond or sulfur atom; $R^5$ represents hydrogen atom, a halogen atom, an alkyl group, a haloalkyl group, an aryl group, an alkoxy group, an aryloxy group, an alkoxycarbonyl group, a carbamoyl group, a sulfamoyl group, an acylamino group, a sulfonylamino group, cyano group, hydroxyl group, or nitro group; $R^6$ represents hydrogen atom, an alkyl group, an acyl group, a sulfonyl group, an alkoxycarbonyl group, a sulfamoyl group, or a carbamoyl group; n represents an integer of 1, 2 or 3, and when n represents 2 or 3, two or three $R^5$ which may be the same or different substitute on the benzene ring, respectively; L represents a linking group selected from a group consisting of a $C_{2-12}$ alkylene group, and an alkylene group containing one or more phenylene groups or ether groups and having 4–12 atoms that constitute a full length of a linking chain; and Q represents a substituted or unsubstituted 5- or 6-membered heterocyclic group, or a substituted or unsubstituted condensed heterocyclic group containing 8–10 ring-membered atoms.

The present invention further provides methods for preparing the compounds represented by the above formula (IA) or (IB), medicaments comprising the compounds represented by the above formula (IA) or (IB), and methods for manufacturing the medicaments comprising the compounds represented by the above formula (IA) or (IB). As a preferred embodiment of the medicament of the present invention, there is provided a pharmaceutical composition which comprises the aforementioned compound as an active ingredient together with a pharmaceutical additive. The pharmaceutical compositions of the present invention are useful as, for example, a preventive and/or therapeutic medicament for hyperlipemia, a preventive and/or therapeutic medicament for arterial sclerosis, an agent for suppressing foaming of macrophages, an agent for retracting arterial sclerosis lesions, an agent for inhibiting the formation of arterial sclerosis lesions, a cholesterol-lowering agent and the like. Use of the compounds represented by the above formula (IA) or (IB) for the manufacture of the aforementioned pharmaceutical composition is also provided as an aspect of the present invention.

According to further aspects of the present invention, there are provided a method for preventive and/or therapeutic treatment of a disease selected from a group consisting of hyperlipemia and arterial sclerosis, which comprises the step of administering a preventively or therapeutically effective amount of the compound represented by the above formula (IA) or (IB) to a patient, and a method for preventive and/or therapeutic treatment of a disease caused by the foaming of macrophages, which comprises the step of administering a preventively or therapeutically effective amount of the compound represented by the above formula (IA) or (IB) to a patient.

Best Mode for Carrying out the Invention

In the above formula (IA), Y represents a single bond or sulfur atom. When Y represents a single bond, the carbon atom between the two nitrogen atoms of the imidazole ring to which $R^3$ binds (2-position carbon atom of the benzimidazole ring) directly binds to the linking group L. Among them, Y is preferably sulfur atom. Z represents oxygen atom, sulfur atom, or N—$R^4$, thereby a condensed heterocyclic ring containing Z represents benzoxazole, benzothiazole, or benzimidazole ring.

$R^1$ and $R^2$ independently represent a hydrogen atom, a halogen atom, an alkyl group, an aryl group, an alkoxy group, an aryloxy group, an alkoxycarbonyl group, carbamoyl group, sulfamoyl group, an acylamino group, a sulfonylamino group, cyano group, hydroxyl group, or nitro group, and n and m independently represent an integer of 1,2, or 3. It is preferred that $R^1$ and $R^2$ independently represent hydrogen atom, a halogen atom, an alkyl group, an alkoxy group, an acylamino group, sulfonylamino group, or an alkoxycarbonyl group, and it is particularly preferred that they independently represent hydrogen atom, chlorine atom, a $C_{1-4}$ alkyl group, or a $C_{1-4}$ alkoxy group. When Z is N—$R^4$, it is preferred that either of $R^1$ and $R^2$ is hydrogen atom.

When n represents 1, the definition means that one $R^1$ substitutes at an arbitrary position of the benzene ring. When n represents 2 or 3, the definition means that two or three $R^1$ groups substitute at arbitrary positions of the benzene ring. When n represents 2 or 3, two or three $R^1$ groups may be the same or different. Similarly, when m represents 1, the definition means that one $R^2$ substitutes at an arbitrary position of the benzene ring, and when n represents 2 or 3, the definition means that two or three $R^2$ groups substitute at arbitrary positions of the benzene ring. When n represents 2 or 3, two or three $R^2$ groups may be the same or different. It is preferred that $R^1$ and $R^2$ substitute at 5- and/or 6-positions of the condensed heterocyclic ring containing the benzimidazole ring and the heterocyclic ring containing Z, respectively.

Specific examples of substituents represented by $R^1$ and $R^2$ will be explained below. As the halogen atom, fluorine atom, chlorine atom, bromine atom, or iodine atom may be used, and preferably fluorine atom, chlorine atom, or bromine atom may be used. Chlorine atom may most preferably be used. As the alkyl group, a straight-chain, branched-chain, or cyclic $C_{1-18}$ (containing 1–18 carbon atoms) alkyl group may be used. For example, methyl group, ethyl group, n-propyl group, isopropyl group, n-butyl group, sec-butyl group, tert-butyl group, cyclopropyl group, cyclohexyl group, n-octyl group, n-dodecyl group and n-octadecyl group may be used. Preferably, a straight-chain, branched-chain, or cyclic-$C_{1-8}$ alkyl group, and more preferably, a straight-chain or branched-chain $C_{1-4}$ alkyl group may be used. Methyl group may most preferably be used.

Examples of the haloalkyl group include those having one or more halogen atoms, which may be the same or different, substituted on the aforementioned straight-chain, branched-chain, or cyclic $C_{1-8}$ alkyl group, preferably the straight-chain, branched, or cyclic $C_{1-8}$ alkyl group, more preferably the straight-chain or branched $C_{1-4}$ alkyl group. As the halogen atom, for example, fluorine atom or chlorine atom, more preferably fluorine atom may be used. For example, monochloromethyl group, trifluoromethyl group, 2,2,2-trifluoroethyl group, pentafluoroethyl group or the like may be used, and most preferably, trifluoromethyl group may be used.

Examples of the aryl group include a substituted or unsubstituted $C_{6-14}$ aryl group such as a substituted or unsubstituted phenyl group or a substituted or unsubstituted naphthyl group. Preferably, a substituted or unsubstituted phenyl group, and more preferably, unsubstituted phenyl group may be used. Examples of a substituent of the aryl group include the alkyl group, the haloalkyl group, and the halogen mentioned above, hydroxyl group, alkoxy groups mentioned below and the like. As the aryloxy group, a $C_{6-14}$ aryloxy group formed by substituting one hydrogen atom on a ring of the above aryl groups with oxygen atom may be used. For example, phenoxy group, 1-naphthyloxy group, 2-naphthyloxy group or the like may be used.

As the alkoxy group, straight-chain, branched-chain, or cyclic $C_{1-18}$ alkoxy group may be used. For example, methoxy group, ethoxy group, n-propoxy group, isopropoxy group, n-butoxy group, sec-butoxy group, tert-butoxy group, cyclohexyloxy group, n-octyloxy group, n-dodecyloxy group and n-octadecyloxy group may be used. Preferably, a straight-chain, branched-chain, or cyclic $C_{1-8}$ alkoxy group, and more preferably, a straight-chain or branched-chain $C_{1-4}$ alkoxy group, and most preferably, methoxy group or ethoxy group may be used. Examples of the alkoxycarbonyl group include carbonyl groups substituted with the aforementioned straight-chain, branched-chain, or cyclic $C_{1-18}$ alkoxy group, preferably a straight-chain, branched-chain, or cyclic-$Cl_{1-8}$ alkoxy group, and more preferably a straight-chain or branched-chain $C_{1-4}$ alkoxy group. For example, methoxycarbonyl group, ethoxycarbonyl group, n-butoxycarbonyl, tert-butoxycarbonyl group, n-octyloxycarbonyl group, n-dodecyloxycarbonyl group, n-octadecyloxycarbonyl group or the like, and preferably methoxycarbonyl group or ethoxycarbonyl group may be used.

As the carbamoyl group, a substituted or unsubstituted carbamoyl group may be used, and as the substituted carbamoyl group, a mono- or disubstituted carbamoyl group may be used. As one or two functional groups substituting on the carbamoyl group, for example, the aforementioned $C_{1-18}$ alkyl groups or the aforementioned $C_{6-14}$ aryl groups may be used. It is desirable that the total number of carbon atoms contained in the one or two functional groups may be 18 or less, preferably 12 or less, and more preferably 6 or less. Examples of the substituted carbamoyl group include methylcarbamoyl group, diethylcarbamoyl group, n-octylcarbamoyl group, n-hexadecylcarbamoyl group and phenylcarbamoyl group, preferably methylcarbamoyl group or the like.

As the sulfamoyl group, a substituted or unsubstituted sulfamoyl group may be used, and as the substituted sulfamoyl group, a mono- or disubstituted sulfamoyl group may be used. As one or two functional groups substituting on the sulfamoyl group, for example, the aforementioned $C_{1-18}$ alkyl groups or the aforementioned $C_{6-14}$ aryl groups may be used. It is desirable that the total number of carbon atoms contained in the one or two functional groups may be 18 or less, preferably 12 or less, and more preferably 6 or less. As the substituted sulfamoyl group, for example, methylsulfamoyl group, diethylsulfamoyl group, n-octylsulfamoyl group, n-hexadecylsulfamoyl group, phenylsulfamoyl group or the like, and preferably methylsulfamoyl group may be used.

As an acyl group constituting the acylamino group, an alkylcarbonyl group comprising carbonyl group substituted with the aforementioned $C_{1-18}$ alkyl group, a haloalkylcarbonyl group having the aforementioned halo-$C_{1-18}$ alkyl group, or an arylcarbonyl group having the aforementioned $C_{6-14}$ aryl group may be used. It is desirable that the number of carbon atoms of the alkyl group, haloalkyl group, or aryl group which substitutes on the carbonyl group may preferably be 12 or less, and more preferably 6 or less. As the acylamino group, for example, acetylamino group, trifluoroacetylamino group, propionylamino group, n-butanoylamino group, n-octanoylamino group, n-hexadecanoylamino group, benzoylamino group or the like, preferably, acetylamino group or propionylamino group, and most preferably, propionylamino group may be used.

As sulfonyl group constituting the sulfonylamino group, an alkylsulfonyl group comprising sulfonyl group substituted with the aforementioned $C_{1-18}$ alkyl group, a haloalkylsulfonyl group having the aforementioned halo-$C_{1-18}$ alkyl group, an arylsulfonyl group having the aforementioned $C_{6-14}$ aryl groups may be used. It is desirable that the number of carbon atoms of the alkyl group, haloalkyl group, or aryl group which substitute on the sulfonyl group may preferably be 12 or less, and more preferably 6 or less. As the sulfonylamino group, for example, methanesulfonylamino group, trifluoromethanesulfonylamino group, ethanesulfonylamino group, n-butane-sulfonylamino group, n-octanesulfonylamino group, n-hexadecanesulfonylamino group, benzenesulfonylamino group, p-toluenesulfonylamino group or the like, and preferably, methanesulfonylamino group may be used.

$R^3$ and $R^4$ independently represent hydrogen atom, an alkyl group, an acyl group, a sulfonyl group, an alkoxycarbonyl group, a sulfamoyl group, or a carbamoyl group. As the alkyl group represented by $R^3$ and $R^4$, the aforementioned $C_{1-18}$ alkyl group may be used. Among them, preferably a straight-chain or branched-chain group, more preferably a straight-chain or branched-chain $C_{1-8}$ alkyl group, further preferably a straight-chain or branched-chain $C_{1-4}$ alkyl group, and most preferably methyl may be used. As the acyl group represented by $R^3$ and $R^4$, an alkylcarbonyl group comprising carbonyl group substituted with the aforementioned $C_{1-18}$ alkyl group, a haloalkylcarbonyl group having the aforementioned halo-$C_{1-18}$ alkyl group, an arylcarbonyl group having the aforementioned $C_{6-14}$ aryl groups may be used.

As the sulfonyl group represented by $R^1$ and $R^4$, an alkylsulfonyl group comprising sulfonyl group substituted with the aforementioned $C_{1-18}$ alkyl group, haloalkylsulfonyl group having the aforementioned halo-$C_{1-18}$ alkyl group, an arylsulfonyl group having the aforementioned $C_{6-14}$ aryl group may be used. As the alkoxycarbonyl group, carbonyl group substituted with the aforementioned $C_{1-18}$ alkoxy group, preferably a $C_{1-8}$ alkoxy group, more preferably a straight-chain or branched-chain $C_{1-4}$ alkoxy group may be used. As the carbamoyl group and the sulfamoyl group, the substituted or unsubstituted carbamoyl groups and sulfamoyl groups explained above may be used. It is preferred that $R^3$ and $R^4$ independently represent hydrogen atom, a straight-chain or branched-chain $C_{1-5}$ alkyl group, a straight-chain or branched-chain $C_{1-4}$ alkylcarbonyl group or the like. Most preferably, $R^1$ and $R^4$ are hydrogen atoms.

In the above formula (IA), L represents a linking group, and this linking group is selected from L represents a linking group selected from a group consisting of a $C_{2-12}$ alkylene group, and an alkylene group containing one or more phenylene groups or ether groups and having 4–12 atoms that constitute a full length of a linking chain. These alkylene groups may be substituted with other substituents, and the alkylene may be a straight-chain or branched-chain. As the $C_{2-12}$ alkylene group, for example, ethylene group, 1,4-butylene group, 1,5-pentylene group, 1,6-hexylene group, 1,10-decylene group or the like may be used. Preferably, a straight-chain or branched-chain $C_{4-12}$ alkylene group, more preferably a straight-chain or branched-chain $C_{4-11}$ alkylene group, further preferably a linear $C_{4-8}$ alkylene group, and most preferably a $C_{5-6}$ alkylene group may be used.

When L contains one or more phenylene groups or ether groups, number of carbon atoms and oxygen atoms constituting a chain moiety of the linking group (these atoms are referred to as "atoms constituting a full length of a linking chain") are from 4 to 12 (for phenylene group, the numbers of the atoms is considered as 4). The phenylene group may have one or more substituents which may be the same or different and selected from, for example, those explained above as to $R^1$, e.g., an alkyl group, a haloalkyl group, a halogen atom, an alkoxy group, hydroxyl group and the like.

Examples of the linking group containing phenylene group include, for example, alkylene-phenylene-alkylene groups such as 1,4-xylylene group, 1,3-xylylene group, 1,2-xylylene group, and 2-ethylene-4-phenylmethyl group, and examples of the linking group containing ether group include, for example, ethylyleneoxyethyl group and ethyleneoxyethoxyethyl group. L is preferably a $C_{4-8}$ alkylene group or ethyleneoxyethyl group, and most preferably a $C_{5-6}$ alkylene group. In the compounds of the present invention represented by the formula (IA), the two partial moiety that are bound by means of the linking group L (the right partial structure and the left partial structure bridged with L in the formula (IA)) are not identical to each other. In addition, when Y is sulfur atom, Z is N—$R^4$, n=m, and $R^3$ and $R^4$ are the same substituents, $R^1$ and $R^2$ do not represent identical substituents. More preferably, where Y is sulfur atom, Z is N—$R^4$, and n=m, $R^1$ and $R^4$ do not represent identical substituents when $R^1$ and $R^2$ are the same substituents.

As preferred compounds represented by the formula (IA), there are provided:

(a) the aforementioned compounds wherein Y represents a single bond or sulfur atom; Z represents oxygen atom, sulfur atom or N—$R^4$; $R^1$ and $R^2$ independently represent hydrogen atom, a halogen atom, an alkyl group, a haloalkyl group, an aryl group, an alkoxy group, an alkoxycarbonyl group, a sulfamoyl group, an acylamino group, a sulfonylamino group, cyano group, hydroxyl group, or nitro group; $R^3$ and $R^4$ independently represent hydrogen atom, an alkyl group, or an acyl group; n and m independently represent 1 or 2; and L represents a linking group selected from a $C_{4-11}$ alkylene group, or an alkylene group containing one or more ether groups and having 5–8 atoms constituting a full length of a linking chain;

(b) the aforementioned compounds wherein Y represents a single bond or sulfur atom; Z represents oxygen atom, sulfur atom or N—$R^4$; $R^1$ and $R^2$ independently represent hydrogen atom, a halogen atom, a $C_{1-4}$ alkyl group, a halo-$C_{1-4}$ alkyl group, phenyl group, a $C_{1-4}$ alkoxy group, a $C_{1-4}$ alkoxycarbonyl group, a $C_{1-4}$ alkylsulfamoyl group, a $C_{1-4}$ alkylcarbonylamino group, a $C_{1-4}$ alkylsulfonylamino group, cyano group, hydroxyl group, or nitro group; $R^3$ and $R^4$ independently represent hydrogen atom, a $C_{1-4}$ alkyl group, or an $C_{1-4}$ alkylcarbonyl group; n and m independently represent 1 or 2; and L represents a linking group selected from a $C_{4-11}$ alkylene group, or an alkylene group containing one or more ether groups and having 5–8 atoms constituting a full length of a linking chain;

(c) the aforementioned compounds wherein Y represents a single bond or sulfur atom; $R^1$ represents hydrogen atom, a halogen atom, a $C_{1-4}$ alkyl group, or nitro group; n represents 1 or 2; $R^2$ represents hydrogen atom, a halogen atom, a $C_{1-4}$ alkyl group, a halo-$C_{1-4}$ alkyl group, phenyl group, a $C_{1-4}$ alkoxy group, a $C_{1-4}$ alkoxycarbonyl group, a $C_{1-4}$ alkylsulfamoyl group, a $C_{1-4}$ alkylcarbonylamino group, a $C_{1-4}$ alkylsulfonylamino group, cyano group, or hydroxyl group; m represents 1 or 2; $R^3$ represents hydrogen atom, a $C_{1-4}$ alkyl group or a $C_{1-4}$ alkylcarbonyl group; Z represents oxygen atom, sulfur atom or N—$R^4$ wherein $R^4$ represents hydrogen atom, a $C_{1-4}$ alkyl group, or a $C_{1-4}$ alkylcarbonyl group; and L represents a linking group selected from a $C_{4-11}$ alkylene group and an alkylene group containing one or more ether groups and having 5–8 atoms constituting a full length of a linking chain;

(d) the aforementioned compounds according to the above (c), wherein $R^2$ is hydrogen atom when Y represents a single bond;

(e) the aforementioned compounds according to the above (c) or (d), wherein Y is sulfur atom when L represents an alkylene group containing one or more ether groups and having 5–8 atoms constituting a full length of a linking chain;

(f) the aforementioned compounds according to the above (e), wherein $R^1$ represents a halogen atom; n represents 1 or 2; $R^2$ represents a halogen atom; and m represents 1 or 2;

(g) the aforementioned compounds according to the above (e), wherein $R^1$ represents a halogen atom; n represents 1 or 2; $R^2$ represents a halogen atom; and m represents 2; and (h) each of the aforementioned compounds, wherein $R^1$ and $R^2$ are substituents at 5- and/or 6-position of the respective condensed heterocyclic rings.

Among the compounds of the above formula (IA), examples of the most preferred compounds according to the present invention include each of the compounds wherein, as to the substituents represented by $R^1$ and/or $R^2$, the halogen atom is chlorine atom, the $C_{1-4}$ alkyl group is methyl group, the halo-$C_{1-4}$ alkyl group is trifluoromethyl group, the $C_{1-4}$ alkoxy group is methoxy group or ethoxy group, the $C_{1-4}$ alkoxycarbonyl group is ethoxycarbonyl group, the $C_{1-4}$ alkylsulfamoyl group is methylsulfamoyl group, the $C_{1-4}$ alkylcarbonylamino group is ethylcarbonylamino group, and the $C_{1-4}$ alkylsulfonylamino group is methylsulfonylamino group; and as to the substituents represented by $R^3$ and/or $R^4$, the $C_{1-4}$ alkyl group is methyl group, the $C_{1-4}$ alkylcarbonyl group is ethylcarbonyl group, and the alkylene group containing one or more ether groups and having 5–8 atoms constituting a full length of a linking chain represented by L is ethylyleneoxyethyl group or ethyleneoxyethoxyethyl group.

Among the compounds of the present invention represented by the formula (IA), Compounds A1 to Compound A39 are shown below as examples of particularly preferred compounds. However, the scope of the present invention is not limited to these compounds.

(1)

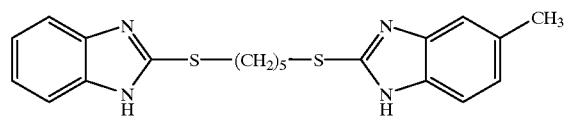

(2)

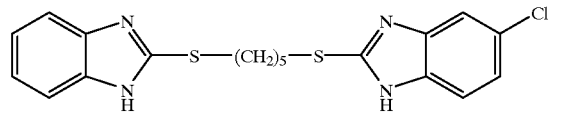

(3)

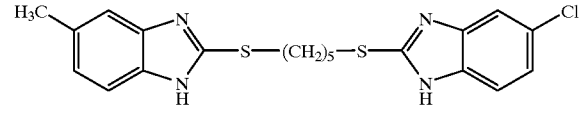

(4)

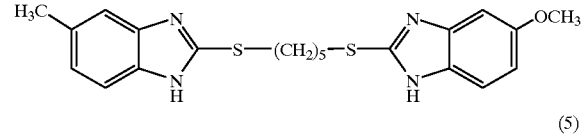

(5)

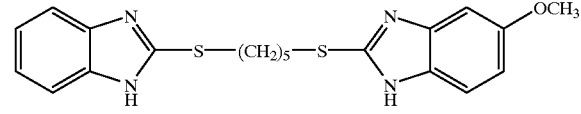

(6)

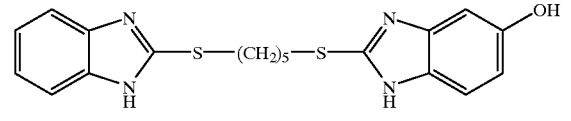

(7)

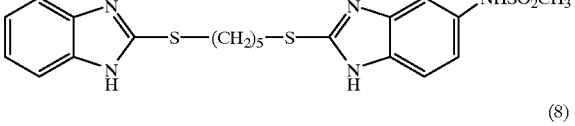

(8)

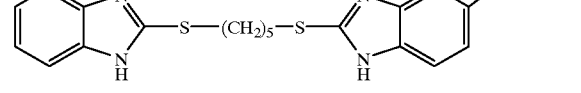

-continued (9) — Benzimidazole-S-(CH₂)₅-S-benzimidazole-COOC₂H₅

(10) — Benzimidazole-S-(CH₂)₅-S-5,6-dimethylbenzimidazole

(11) — Benzimidazole-S-(CH₂)₅-S-5,6-dichlorobenzimidazole

(12) — Benzimidazole-S-(CH₂)₆-S-5,6-dichlorobenzimidazole

(13) — Benzimidazole-S-(CH₂)₈-S-5,6-dichlorobenzimidazole

(14) — 5-methylbenzimidazole-S-(CH₂)₅-S-5,6-dichlorobenzimidazole

(15) — 5,6-dimethylbenzimidazole-S-(CH₂)₅-S-5,6-dichlorobenzimidazole

(16) — Benzimidazole-S-(CH₂)₅-S-5-chloro-6-trifluoromethylbenzimidazole

(17) — Benzimidazole-S-(CH₂)₅-S-5-cyanobenzimidazole

(18) — Benzimidazole-S-(CH₂)₄-S-5-methylbenzimidazole

(19) — Benzimidazole-S-(CH₂)₆-S-5-methylbenzimidazole

(20) — Benzimidazole-S-(CH₂)₈-S-5-methylbenzimidazole

(21) — Benzimidazole-S-(CH₂)₂O(CH₂)₂-S-5-methylbenzimidazole

(22) — Benzimidazole-S-(CH₂)₂O(CH₂)₂O(CH₂)₂-S-5-methylbenzimidazole

(23) — Benzimidazole-S-(CH₂)₅-S-(1-methyl-5-SO₂NHCH₃-benzimidazole)

(24) — (1-COC₂H₅-benzimidazole)-(CH₂)₅-S-(1-COC₂H₅-benzimidazole)

(25) — (1-COC₂H₅-benzimidazole)-S-(CH₂)₅-S-(1-methyl-5-SO₂NHCH₃-benzimidazole)

(26) — (1-methylbenzimidazole)-(CH₂)₅-S-(1-methylbenzimidazole)

(27) — Benzimidazole-(CH₂)₅-S-benzimidazole

(28) — 5,6-dimethylbenzimidazole-(CH₂)₅-S-benzimidazole

-continued

(29) 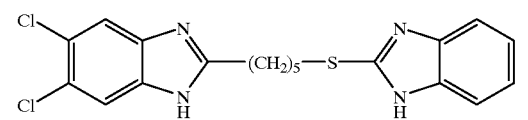

(30) 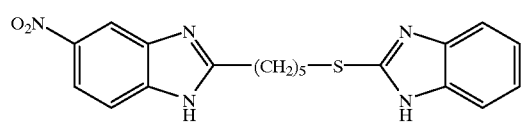

(31) 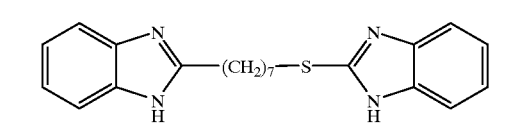

(32) 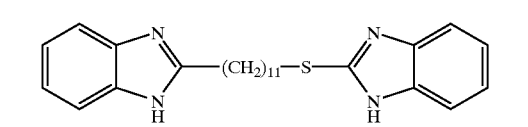

(33) 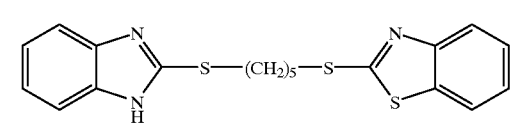

(34) 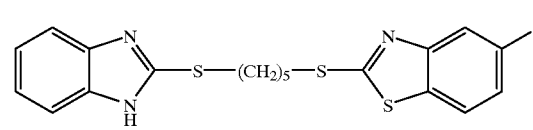

(35) 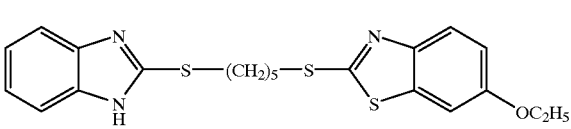

(36) 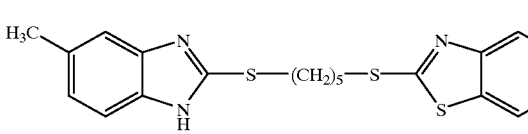

(37) 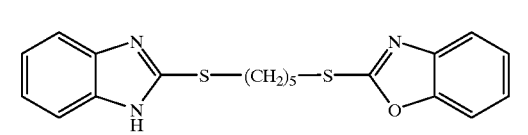

(38) 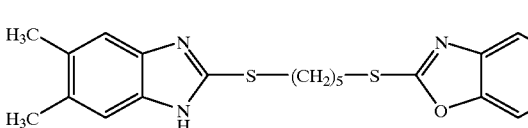

(39) 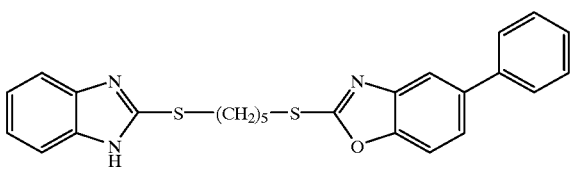

In the aforementioned formula (IB) according to the second aspect of the present invention, Y represents a single bond or sulfur atom. When Y represents a single bond, the carbon atom between the two nitrogen atoms of the imidazole ring to which $R^6$ binds (the carbon atom at the 2-position of the benzimidazole ring) is directly bound to the linking group L. Y is preferably sulfur atom.

$R^5$ represents hydrogen atom, a halogen atom, an alkyl group, a haloalkyl group, an aryl group, an alkoxy group, an aryloxy group, an alkoxycarbonyl group, a carbamoyl group, a sulfamoyl group, an acylamino group, a sulfonylamino group, cyano group, hydroxyl group, or nitro group, and n represents an integer of 1, 2 or 3. $R^5$ preferably represents hydrogen atom, a halogen atom, an alkyl group, an alkoxy group, an alkoxycarbonyl group, a carbamoyl group, a sulfamoyl group, an acylamino group, a sulfonylamino group, or nitro group. $R^5$ most preferably represents hydrogen atom, chlorine atom, a $C_{1-4}$ alkyl group, a $C_{1-4}$ alkoxy group, a $C_{1-4}$ alkoxycarbonyl group, a substituted or unsubstituted carbamoyl group, a substituted or unsubstituted sulfamoyl group, an acylamino group, sulfonylamino group, or nitro group.

When n represents 1, the definition means that one $R^5$ substitutes at an arbitrary position of the benzene ring. When n represents 2 or 3, the definition means that two or three $R^5$ groups substitute at arbitrary positions of the benzene ring. When n represents 2 or 3, two or three $R^5$ groups may be the same or different. It is preferred that one or two $R^5$ substitute at 5- and/or 6- positions of the benzimidazole ring. As the substituent represented by $R^5$, i.e., a halogen atom, an alkyl group, a haloalkyl group, an aryl group, an aryloxy group, an alkoxy group, an alkoxycarbonyl group, a carbamoyl group, a sulfamoyl group, an acyl group constituting an acylamino group, and a sulfonyl group constituting a sulfonylamino group, those specifically explained above as to $R^1$ and $R^2$ may be used.

$R^6$ represents hydrogen atom, an alkyl group, an acyl group, a sulfonyl group, an alkoxycarbonyl group, a sulfamoyl group, or a carbamoyl group, and as the functional groups, those specifically explained above as to $R^3$ and $R^4$ may be used. $R^6$ preferably represents hydrogen atom, a straight-chain or branched-chain $C_{1-5}$ alkyl group, a straight-chain or branched-chain $C_{1-4}$ alkylcarbonyl group or the like, and most preferably represents hydrogen atom.

In the above formula (IB), L represents a linking group, and the linking group is selected from a $C_{2-12}$ alkylene group, or an alkylene group containing one or more phenylene groups or ether groups and having 4–12 atoms constituting a full length of a linking chain. As these linking group, those specifically explained as L of the compounds of the formula (IA) may be used.

Q represents a 5- or 6-membered heterocyclic group, or a condensed heterocyclic group containing 8–10 ring-membered atoms. These heterocyclic groups may be substituted or unsubstituted. Numbers of hetero atoms contained in the above heterocyclic ring is not particularly limited so long as the ring contains at least one hetero atom, and the ring may be constituted only by heteroatoms. The sort of the hetero atoms is not particularly limited. For example, nitrogen atom, sulfur atom, oxygen atom or the like may be used.

The heterocyclic ring that constitutes the 5- or 6-membered heterocyclic group may be either saturated or unsaturated. For example, pyridine (e.g., 2-pyridyl group or 4-pyridyl group), pyrimidine (e.g., 2-pyrimidyl group or 4-pyrimidyl group), pyrazine (e.g., 2-pyrazyl group), piperidine (e.g., 2-piperidyl group), piperazine (e.g., 2-piperazyl group), morpholine (e.g., 2-morpholino group), quinoline (e.g., 2-quinolyl group, 4-quinolyl group, 8-quinolyl group), pyrrole (e.g., 2-pyrrolyl group), thiophene (e.g., 2-thienyl group), furan (e.g., 2-furyl group), imidazole (e.g., 2- imidazolyl group), triazole (e.g., 1,2,4-triazol-3-yl group), tetrazole (e.g., 1,2,3,4-tetrazol-5-yl group), thiazole (e.g., 2-thiazolyl group, 3-isothiazolyl group), thiaziazole (e.g., 2-thiadiazolyl group), oxazole (e.g., 2-oxazolyl group, 3-iso xazolyl group), oxadiazole (e.g., 2-oxadiazolyl group), purine (e.g., 6-purinyl group, 8-purinyl group), pyrazolo[3,4-d]pyrimidine (e.g., 1H-pyrazolo[3,4-d]pyrimidin-4-yl group) or the like.

As the heterocyclic group containing 8–10 ring-membered atoms, those formed by condensation of the aforementioned 5- or 6-membered heterocyclic group with one benzene ring or the aforementioned 5- or 6-membered heterocyclic ring may be used. Where the aforementioned heterocyclic ring or the condensed heterocyclic ring is substituted, examples of the substituent include, for example, a halogen atom, an alkyl group, a haloalkyl group, an aryl group, an alkoxy group, an aryloxy group, an alkoxycarbonyl group, a carbamoyl group, a sulfamoyl group, an acylamino group, and a sulfonylamino group as explained above as to $R^5$; the aforementioned 5- or 6-membered heterocyclic group; nitro group; a substituted or unsubstituted amino group, e.g., amino group, a monoalkylamino group, and a dialkylamino group; hydroxyl group; an alkylthio group which comprises thiol group substituted with the aforementioned alkyl group; an arylthio group which comprises thiol group substituted with the aforementioned aryl group; mercapto group; cyano group; oxo group; thioxo group; oxide group on a nitrogen atom that constitutes a heterocyclic ring; and the aforementioned 5- or 6-membered heterocyclic group and the like.

However, compounds wherein Q represents a substituted or unsubstituted 2-benzimidazolyl group, a substituted or unsubstituted 2-benzoxazolyl group, a substituted or unsubstituted 2-benzothiazolyl group, and a substituted or unsubstituted 4,5-diphenyl-2-imidazolyl group are excluded from the scope of the present invention.

As preferred embodiments of the compounds represented by the formula (IB), there are provided:

(i) the aforementioned compounds, wherein Y represents a single bond or sulfur atom; $R^5$ represents hydrogen atom, a halogen atom, an alkyl group, an alkoxy group, an alkoxycarbonyl group, a carbamoyl group, a sulfamoyl group, an acylamino group, a sulfonylamino group, or nitro group; $R^6$ represent hydrogen atom, an alkyl group, or an acyl group; n represents 1 or 2; and L represents a linking group selected from a $C_{4-11}$ alkylene group or an alkylene group containing one or more ether groups and having 5–8 atoms constituting a full length of a linking chain;

(j) the aforementioned compounds, wherein Y represents a single bond or sulfur atom; $R^5$ represents hydrogen atom, a halogen atom, a $C_{1-4}$ alkyl group, a $C_{1-4}$ alkoxy group, a $C_{1-4}$ alkoxycarbonyl group, a substituted or unsubstituted carbamoyl group, a substituted or unsubstituted sulfamoyl group, an acylamino group, a sulfonylamino group, or nitro group; $R^6$ represents hydrogen atom, a $C_{1-4}$ alkyl group or a $C_{1-4}$ alkylcarbonyl group; n represents 1 or 2; and L represents a linking group selected from a $C_{4-11}$ alkylene group or an alkylene group containing one or more ether groups and having 5–8 atoms constituting a full length of a linking chain;

(k) the aforementioned compounds, wherein Y represents a single bond or sulfur atom; $R^5$ represents hydrogen atom, a halogen atom, a $C_{1-4}$ alkyl group, a $C_{1-4}$ alkoxy group, a $C_{1-4}$ alkoxycarbonyl group, a $C_{1-4}$ alkylcarbamoyl group, a $C_{1-4}$ alkylsulfamoyl group, a $C_{1-4}$ alkylcarbonylamino group, a $C_{1-4}$ alkylsulfonylamino group, or nitro group; $R^6$ represents hydrogen atom, a $C_{1-4}$ alkyl group, or a $C_{1-4}$ alkylcarbonyl group; n represents 1 or 2; and L represents a linking group selected from a $C_{4-11}$ alkylene group or an alkylene group containing one or more ether groups and having 5–8 atoms constituting a full length of a linking chain;

(l) the aforementioned compounds according to the above (k), wherein n represents 2, and two $R^5$ groups substitute at the 5- and 6-positions of the benzimidazole ring;

(m) the aforementioned compounds according to the above (k) or (l), wherein $R^5$ represents hydrogen atom, a halogen atom, a $C_{1-4}$ alkyl group, or nitro group, and $R^6$ represents hydrogen atom when Y represents a single bond;

(n) the aforementioned compounds according to the above (k), wherein Y represents sulfur atom when L represents an alkylene group containing one or more ether groups and having 5–8 atoms constituting a full length of a linking chain;

(o) the aforementioned compounds according to the above (n), wherein $R^5$ represents hydrogen atom; and (p) the aforementioned compounds according to the above (o), wherein Q represents a 5-membered heterocyclic group.

Among the compounds of the above formula (IB), examples of the most preferred compounds according to the present invention include each of the compounds wherein, as to the substituents represented by $R^5$, the halogen atom is chlorine atom, the $C_{1-4}$ alkyl group is methyl group, the $C_{1-4}$ alkoxy group is methoxy group or ethoxy group, the $C_{1-4}$ alkoxycarbonyl group is ethoxycarbonyl group, the $C_{1-4}$ alkylsulfamoyl group is methylsulfamoyl group, the $C_{1-4}$ alkylcarbonylamino group is ethylcarbonylamino group, the $C_{1-4}$ alkylsulfonylamino group is methylsulfonylamino group; and as to the substituents represented by $R^6$, the $C_{1-4}$ alkyl group is methyl group, the $C_{1-4}$ alkylcarbonyl group is ethylcarbonyl group; and the alkylene group containing one or more ether groups and having 5–8 atoms constituting a full length of a linking chain represented by L is ethylyleneoxyethyl group or ethyleneoxyethoxyethyl group.

Among the compounds of the present invention represented by the formula (IB), Compounds B1 to Compound B68 are shown below as examples of particularly preferred compounds. However, the scope of the present invention is not limited to these compounds. Group Q in the compounds set out below should be understood as preferred examples of Q.

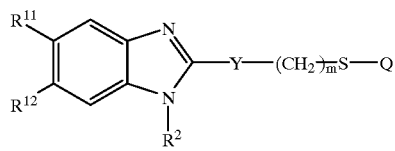
| No. | $R^{11}$ | $R^{12}$ | $R^2$ | Y | m | Q |
|---|---|---|---|---|---|---|
| (1) | H | H | H | S | 5 | 2-imidazolyl (NH) |
| (2) | H | H | H | S | 5 | 1-methyl-2-imidazolyl |
| (3) | H | H | H | S | 5 | 1-phenyl-2-imidazolyl |
| (4) | H | H | H | S | 5 | 1,5-diphenyl-2-imidazolyl |
| (5) | H | H | H | S | 5 | 3-(1,2,4-triazolyl) (NH) |
| (6) | H | H | H | S | 5 | 4-methyl-3-(1,2,4-triazolyl) |
| (7) | H | H | H | S | 5 | 4-phenyl-3-(1,2,4-triazolyl) |
| (8) | H | H | H | S | 5 | 4,5-dimethyl-3-(1,2,4-triazolyl) |
| (9) | H | H | H | S | 5 | 5-acetamido-4-methyl-3-(1,2,4-triazolyl) |
| (10) | H | H | H | S | 5 | 1-methyl-5-tetrazolyl |

-continued
| | | | | | | |
|---|---|---|---|---|---|---|
| (11) | H | H | H | S | 5 | 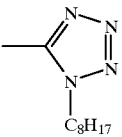 |
| (12) | H | H | H | S | 5 | 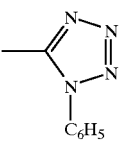 |
| (13) | H | H | H | S | 5 | 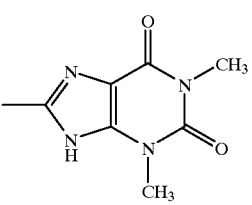 |
| (14) | H | H | H | S | 5 | 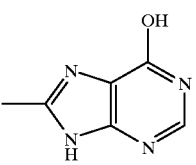 |
| (15) | H | H | H | S | 5 | 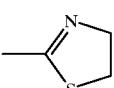 |
| (16) | H | H | H | S | 5 | 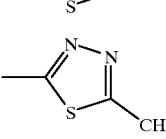 |
| (17) | H | H | H | S | 5 | 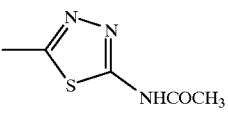 |
| (18) | H | H | H | S | 5 | 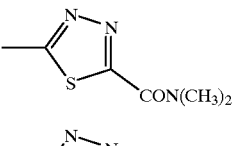 |
| (19) | H | H | H | S | 5 | 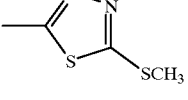 |
| (20) | H | H | H | S | 5 | 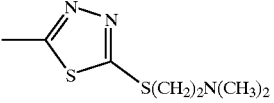 |
| (21) | H | H | H | S | 5 | 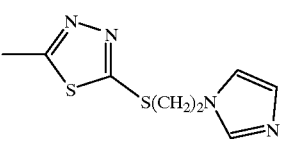 |
| (22) | H | H | H | S | 5 | 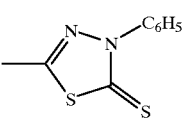 |

-continued
| | | | | | | |
|---|---|---|---|---|---|---|
| (23) | H | H | H | S | 5 | 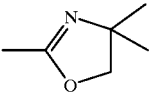 |
| (24) | H | H | H | S | 5 | 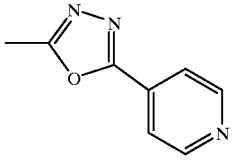 |
| (25) | H | H | H | S | 5 | 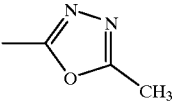 |
| (26) | H | H | H | S | 5 | 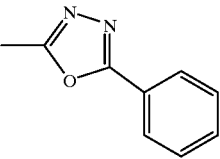 |
| (27) | H | H | H | S | 5 | 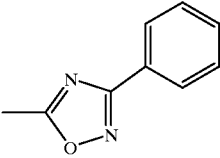 |
| (28) | H | H | H | S | 5 | 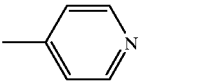 |
| (29) | H | H | H | S | 4 | 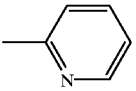 |
| (30) | H | H | H | S | 5 | 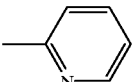 |
| (31) | H | H | H | S | 6 | 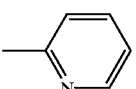 |
| (32) | H | H | H | S | 8 | 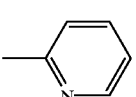 |
| (33) | CH$_3$ | CH$_3$ | H | S | 5 | 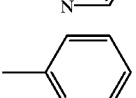 |
| (34) | OCH$_3$ | H | H | S | 5 | 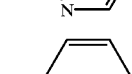 |
| (35) | CH$_3$ | H | H | S | 5 | 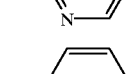 |
| (36) | COOC$_2$H$_5$ | H | H | S | 5 | 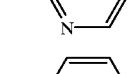 |

-continued
| | | | | | | |
|---|---|---|---|---|---|---|
| (37) | NHCOC$_2$H$_5$ | H | H | S | 5 | 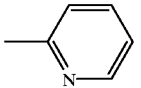 |
| (38) | NHSO$_2$CH$_3$ | H | H | S | 5 | 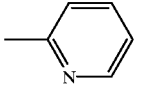 |
| (39) | CON(CH$_3$)$_2$ | H | H | S | 5 | 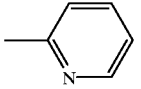 |
| (40) | H | H | H | S | 5 | 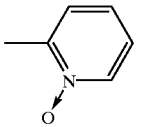 |
| (41) | H | H | H | S | 5 | 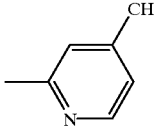 |
| (42) | H | H | H | S | 5 | 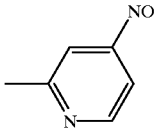 |
| (43) | H | H | H | — | 5 | 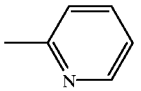 |
| (44) | Cl | Cl | H | — | 5 | 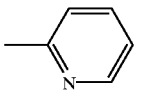 |
| (45) | CH$_3$ | CH$_3$ | H | — | 5 | 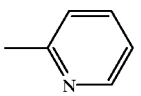 |
| (46) | NO$_2$ | H | H | — | 5 | 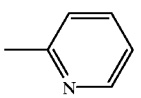 |
| (47) | H | H | H | — | 7 | 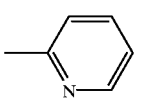 |
| (48) | H | H | H | — | 11 | 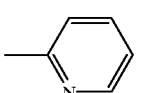 |
| (49) | H | H | H | S | 5 | 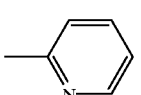 |
| (50) | H | H | H | S | 5 | 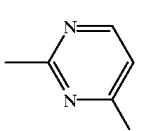 |

-continued

| | | | | | | |
|---|---|---|---|---|---|---|
| (51) | H | H | H | S | 5 | 2,4-dimethylpyrimidin-6-yl |
| (52) | H | H | H | S | 5 | 6-hydroxy-2-methylpyrimidin-4-yl (with CH₃) |
| (53) | H | H | H | S | 5 | 4-hydroxy-6-methylpyridin-2-yl |
| (54) | H | H | H | S | 5 | 1,4,5,6-tetrahydropyrimidin-2-yl |
| (55) | H | H | H | S | 5 | 4,4,6-trimethyl-1,4-dihydropyrimidin-2-yl |
| (56) | H | H | H | S | 5 | 4,6-dimethyl-2-methylthiopyrimidin-... |
| (57) | H | H | H | S | 5 | quinolin-2-yl |
| (58) | Cl | Cl | H | S | 5 | 4-hydroxyquinazolin-2-yl |
| (59) | H | H | H | S | 5 | purin-6-yl |
| (60) | H | H | H | S | 5 | 1H-pyrazolo[3,4-d]pyrimidin-4-yl |

| No. | | | | | | |
|---|---|---|---|---|---|---|
| (61) | H | H | H | S | 5 | [7-propyl-triazolopyrimidine] |
| (62) | H | H | H | S | 5 | [quinolin-8-yl] |
| (63) | H | H | H | S | 5 | [7-CF3-quinolin-4-yl] |
| (64) | H | H | CH$_3$ | S | 5 | [pyridin-2-yl] |
| (65) | H | H | COC$_2$H$_5$ | S | 5 | [pyridin-2-yl] |
| (66) | SO$_2$NHCH$_3$ | H | CH$_3$ | S | 5 | [pyridin-2-yl] |

| No. | R$^{11}$ | R$^{12}$ | R$^2$ | Y | l | Q |
|---|---|---|---|---|---|---|
| (67) | H | H | H | S | 1 | [5-methyl-1,3,4-thiadiazol-2-yl] |
| (68) | H | H | H | S | 2 | [5-methyl-1,3,4-thiadiazol-2-yl] |

The compounds of the present invention represented by the aforementioned formulas (IA) and (IB) may form acid addition salts. In addition, where R$^1$ and/of R$^2$ are hydroxyl groups in the compounds of the formula (IA), or where R$^5$ is hydroxyl group in the compounds of formula (IB), the compounds may form base addition salts. Both of these acid addition salts and base addition salts fall within the scope of the present invention. Furthermore, where R$^1$ and/or R$^2$ are hydroxyl groups in the compounds of the formula (IA), or where R$^5$ is hydroxyl group in the compounds of formula (IB), the compounds may exist as intramolecular zwitterion-type compounds. These compounds also fall within the scope of the present invention. Examples of the acid addition salts include, for example, mineral acid salts such as hydrochlorides, hydrobromides, nitrates, sulfates, or phosphates, or organic acid salts such as p-toluenesulfonates, methanesulfonates, oxalates, tartrates, malates, or citrates. Examples of the base addition salts include, for example, metal salts such as sodium salts, potassium salts, magnesium salts, or calcium salts, ammonium salts, triethylamine salts or the like.

The compounds of the present invention may have one or more asymmetric carbon atoms depending on the sorts of substituents R$^1$ to R$^6$. In that case, optical isomers based on one or more asymmetric carbon atoms or diastereoisomers based on two or more asymmetric carbon atoms may exist, and both of the optical isomers and diastereoisomers in pure forms fall within the scope of the present invention. In addition, any mixtures of the optical isomers in an arbitrary ratio, racemates, and any mixtures the diastereoisomers in an arbitrary ratio also fall within the scope of the present invention. It should also be understood that any hydrate or a solvate of the compound of the present invention in free form or in a form of a salt falls within the scope of the present invention.

The compounds of the present invention can be prepared according to the reaction schemes set out below by reactions well known to those skilled in the art by using a readily available compound of the formula (II) as starting material. Specific methods for the reactions will be detailed in the working examples set cut in the specification. Therefore, those skilled in the art can easily prepare the compounds of the present invention by referring to the general explanation and examples mentioned below, and if necessary, by making suitable alterations and/or modifications to these methods. In the schemes, $R^1$, $R^2$, $R^3$, $R^5$, $R^6$, n, m, Z, Y, and L have the same meanings as those defined above, $X_1$ represents a leaving group for nucleophilic substitution reaction such as a halogen atom or an alkyl- or arylsulfnyloxy group, and $X_2$ represents a leaving group as mentioned above, carboxyl group, or an alkoxycarbonyl group.

potassium carbonate, triethylamine, or sodium ethylate, if necessary. The reaction can also sufficiently proceed in an alcohol by heating without a catalyst. When a base is used, a reaction temperature may be appropriately chosen depending on the sorts of reactants and a solvent. Generally, the reaction may be performed at a temperature of 0–150° C., preferably 20–100° C. When the reaction is carried out in an alcohol without catalyst, a temperature of 50–120° C. is preferable.

When both of $X_1$ and $X_2$ are leaving groups, it is preferred to use an excess amount of compound of the formula (III) based on a compound of the formula (II) in order to avoid any side reactions. Generally, a 2- to 10-fold amount, preferably a 4- to 10-fold amount may be applied. After the completion of the reaction, unreacted compound of the formula (III) can generally be recovered. On the other hand, when $X_2$ is carboxyl group or an alkoxycarbonyl group, an approximately equimolar amount of a compound of the formula (III) should be used based on a compound the formula (II) to avoid side reactions. For example, it is preferable to use an approximately 0.8–1.2 moles, more preferably 0.95–1.1 moles of a compound of the formula (III) based on a compound of the formula (II). When $X_2$ is carboxyl group, a carboxylic acid compound of the formula (IV) produced after the completion of the reaction can be isolated by neutralization and then collection by filtration or extraction with an organic solvent.

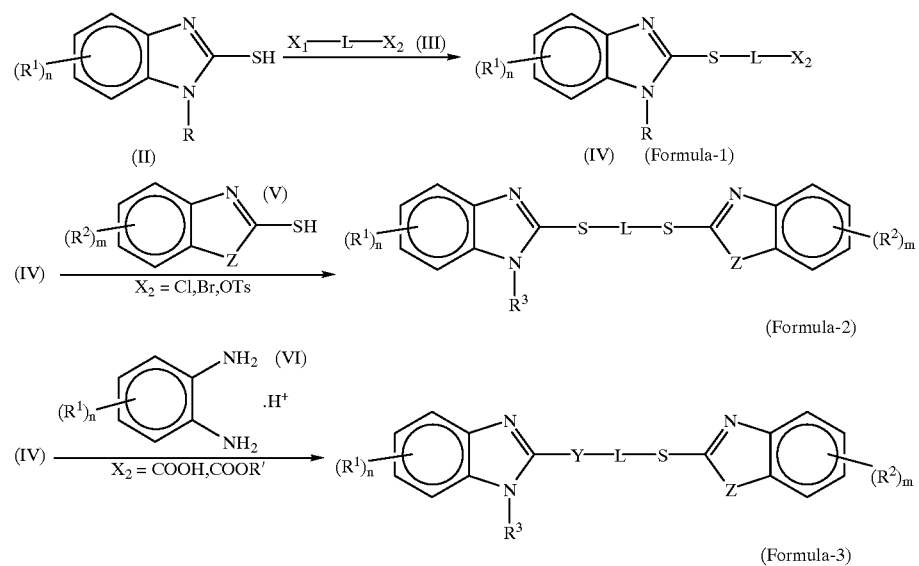

Among the 2-mercaptobenzimidazole compounds of the formula (II) used for the preparation of the compounds of the formula (IV), any compounds already known can be prepared by the methods described in respective literatures. Novel compounds can generally be prepared by the method described in Org. Syn. Col. Vol. 4, p.569. Some of the compounds are commercially available as reagents. A compound of the formula (IV) can be prepared by reacting a compound of the formula (II) with a reagent for introducing a linking group ($X_1$—L—$X_2$: III). This reaction may generally be performed in, for example, in a common organic solvent such as ethanol, acetonitrile, acetone, ethyl acetate, dimethylformamide (DMF), or tetrahydrofuran (THF).

The reaction may be performed in the presence of a base catalyst as an acid scavenger such as sodium hydroxide, When $X_2$ is a leaving group such as chlorine atom, bromine atom, or p-toluenesulfonyloxy group, a compound of the formula (IV) can be subjected to reaction with a 2-mercaptoazole compound of the formula (V) to produce a compound of the formula (IA) of the present invention (a compound of the formula 2 in the above scheme). The compound of the formula (V) used as a reactant in this step can generally be produced by a known method (Org. Syn. Col. Vol., 4, p.569). Some of the compounds can be obtained as commercial products. The reaction between a compound of the formula (IV) and a compound of the formula (V) can be performed under conditions similar to those for the reaction of the compound of the formula (II) and a compound of the formula (III).

When $X_2$ is carboxyl group or an alkoxycarbonyl group, a compound of the formula (IV) can be reacted with an o-phenylenediamine compound of the formula (VI) to prepare a compound of the present invention (a compound of the formula 3 in the scheme). The compound of the formula (VI) can be easily obtained as a commercial product. The condensation-cyclization reaction of a compound of the formula (IV) and a compound of the formula (VI) can generally be performed in the presence of an acid catalyst. As the acid catalyst, for example, hydrochloric acid, hydrobromic acid, sulfric acid, phosphoric acid, an organic sulfonic acid such as p-toluenesulfonic acid or the like can suitably be used. This reaction can be performed without a solvent, or in the presence of water or an organic solvent chosen from various types. A molar ratio of a compound of the formula (VI) based on a compound of the formula (IV) may preferably be 0.8–1.2 and most preferably 0.95–1.1. The acid catalyst can be used in an amount of about 0.1– to 10 moles, preferably 1– to 5 moles based on a compound of the formula (IV).

In the above reactions, when $R^3$ is hydrogen atom, different types of the compounds of the present invention can be produced by subjecting a starting compound of the formula (II) or a compound of the formula 2 or the formula 3 to alkylation or acylation. The alkylation can be performed by reaction with a reactive alkylating agent such as alkyl halides and alkyl tosylates using a base catalyst such as sodium hydroxide, potassium carbonate, triethylamine, or sodium ethylate as an acid scavenger in an ordinary organic solvent as mentioned above. A reaction temperature can be appropriately chosen depending on a type of a compound as a reactant and a solvent. Generally, the reaction is preferably performed at a temperature of about 0–100° C., preferably about 20–60° C.

The acylation can generally be performed by reaction with a corresponding acid halide in the presence of a base catalyst such as potassium carbonate, triethylamine, or pyridine as an acid scavenger in an ordinary inert solvent. As the inert solvent, for example, acetonitrile, ethyl acetate, THF, DMF, dimethylacetamide (DMAc) or the like may be used. When strongly polar DMF, DMAc, acetonitrile or the like is used, the reaction proceeds even in the absence of a base catalyst. The acid halide is preferably used in 1.8– to 2.4 moles based on a compound as a reactant. The reaction may be carried out at a reaction temperature of about 30–150° C., preferably about 50–100° C.

The compounds represented by the formula (IB) can be prepared in a similar manner to the preparation of the compounds represented by the formula (IA). When $X_2$ is a leaving group such as chlorine atom, bromine atom, or p-toluenesulfonyloxy group, a compound of the formula (IV) can be subjected to reaction with a 2-mercapto-substituted heterocyclic compound (VII) to produce a compound of the present invention (a compound of the formula 4 in the above scheme). A compound of the formula (VII) used in this step can generally be produced by a known method, and some of the compounds can be obtained as commercial products. The reaction between a compound of the formula (IV) and a compound of the formula (VII) can be performed in a similar manner to the reaction of a compound of the formula (II) and a compound of the formula (III).

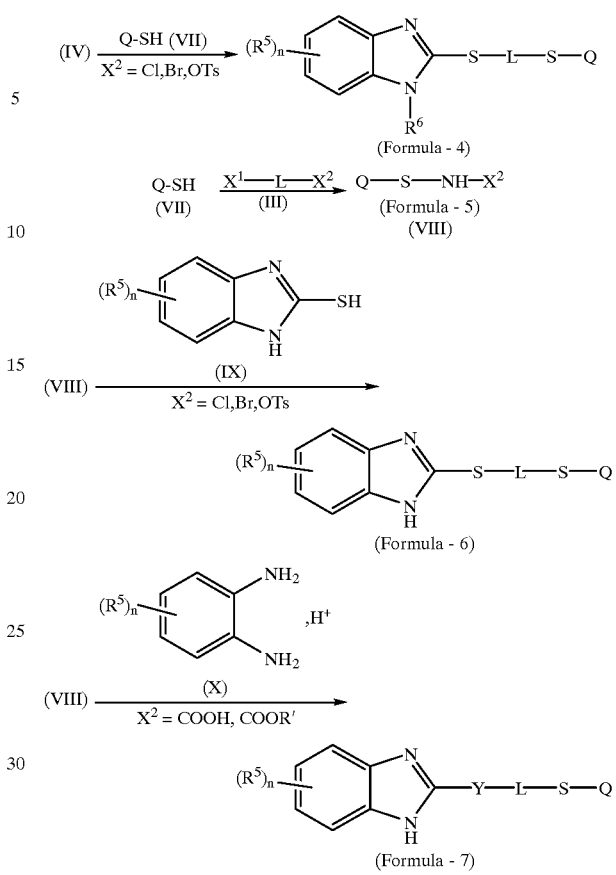

A compound of the formula (VIII), which is obtained by reacting a 2-mercapto-substituted heterocyclic compound of the formula (VII) with an excess amount of an agent (III) for the formation of a linking group according to the scheme mentioned above, may be used as a synthetic intermediate for the preparation of the compound of the present invention. The above reaction for the preparation of a compound of the formula (VIII) can be performed in a similar manner to the reaction of compounds of the formula (II) and the formula (III). When $X^2$ is a halogen atom or an alkyl- or arylsulfonyloxy group, a compound of the present invention can be produced by reacting a compound of the formula (VIII) with a 2-mercaptobenzimidazole of the formula (IX). This reaction can be carried out in a similar manner to the reaction of compounds of the formula (IV) and the formula (V). A 2-mercaptobenzimidazole compound of the formula (IX) can be prepared by a known method, and some of the compounds can be obtained as commercial products.

When $X_2$ is carboxyl group or an alkoxycarbonyl group, a compound of the present invention can be prepared by reacting a compound of the formula (VIII) with an o-phenylenediamine of the formula (X). This reaction can be performed in a similar manner to the reaction of a compound of the formula (IV) and an o-phenylenediamine of the formula (VI). In this reaction, when $R^6$ is hydrogen atom, other compounds of the present invention can be produced by subjecting a starting compound of the formula (II), or a compound of the formula 4, 6 or 7 to alkylation or acylation reaction. The alkylation and the acylation reaction can be performed as described above.

The compounds of the present invention have a potent activity of suppressing the foaming of macrophages which is involved in the formation of arterial sclerosis lesions in arterial sclerosis. Therefore, the compounds are useful as an active ingredient of a medicament for preventive and/or therapeutic treatment of arterial sclerosis, and an active ingredient of a medicament for preventive and/or therapeutic treatment of hyperlipemia by lowering blood cholesterol. According to further aspects of the present invention, there are thus provided a preventive and/or therapeutic medicament for arterial sclerosis, and preventive and/or therapeutic medicament for hyperlipemia each contains the aforementioned compound as an active ingredient.

Although it is not intended to be bound by any specific theory, it has been known that invasion of foamed macrophages into arterial walls triggers hyperplasia of smooth muscles of arterial walls, thereby causing arterial sclerosis (Schaffner, T. et al., Amer. J. Pathol., 110, pp.57–73, 1980; Gerrity, R. G., Amer. J. Pathol. 103, pp.181–190, 1981). The medicaments of the present invention directly inhibit the formation of arterial sclerosis lesions and enables retraction of arterial sclerosis lesions by suppressing the foaming of macrophages which is involved in the formation of arterial sclerosis lesions. Accordingly, the medicaments of the present invention are useful for prevention and/or treatment of arterial sclerosis and hyperlipemia brought by various causes.

Route of administration of the medicament of the present invention is not particularly limited, and the medicament can be administered orally or parenterally. The compound of the formula (IA) or (IB) as an active ingredient, per se, can be used as the medicament of the present invention. Generally, however, it is preferred that pharmaceutical preparations in forms well known to those skilled in the art are provided in which a compound of the formula (IA) or (IB) as active ingredient is added with a pharmacologically and pharmaceutically acceptable additive. Examples of formulations suitable for oral administration include, for example, tablets, capsules, powders, subtilized granules, granules, liquids, syrups and the like. Examples of formulations suitable for parenteral administration include, for example, injections, drip infusions, suppositories, inhalants, formulations for percutaneous absorption, formulations for transmucosal absorption, patches and the like. Examples of pharmacologically and pharmaceutically acceptable additives include excipients, disintegrators or disintegrating agents, binders, lubricants, coating agents, colorants, diluents, base materials, dissolving agents or dissolving aids, isotonic agents, pH modifiers, stabilizers, propellants, adhesives and the like.

Pharmaceutical preparations suitable for oral, percutaneous, or transmucosal administration can be manufactured by using, as pharmacologically or pharmaceutically acceptable additives, for example, excipients such as glucose, lactose, D-mannitol, starch, or crystalline cellulose; disintegrators or disintegrating aids such as carboxymethylcellulose, starch or carboxymethylcellulose calcium; binders such as hydroxypropylcellulose, hydroxypropylmethylcellulose, polyvinylpyrrolidone, or gelatin; lubricants such as magnesium stearate or talc; coating agents such as hydroxypropylmethylcellulose, saccharose, polyethylene glycol, or titanium oxide; base materials such as petrolatum, liquid paraffin, polyethylene glycol, gelatin, china clay, glycerin, purified water, or hard fat; propellants such as flons, diethyl ether, or compressed gases; adhesives such as sodium polyacrylate, polyvinyl alcohol, methylcellulose, polyisobutylene, or polybutene; base cloths such as cotton cloth and plastic sheets, and the like.

Pharmaceutical compositions suitable as injections and drip infusions may contain pharmaceutical additives, for example, dissolving agents or dissolving aids such as distilled water for injection, physiological saline and propylene glycol which can form aqueous injections or injections to be dissolved upon use; isotonic agents such as glucose, sodium chloride, D-mannitol and glycerin; pH modifiers such as inorganic acids, organic acids, inorganic bases, and organic bases and the like.

Dose of the medicament of the present invention is not particular limited, and a dose can be appropriately chosen depending on the route of administration, purpose of preventive and/or therapeutic treatment, age, body weight, and symptoms of a patient and the like. For example, a dose for intravenous administration for an adult may be about 10–400 mg, preferably about 10–100 mg per day as an active ingredient, and for oral administration, a dose for an adult may be about 10–800 mg, preferably about 10–300 mg per day as an active ingredient. The medicament of the present invention may be administered once a day or several times a day as divided portions. Administration period can also be appropriately chosen depending on the age of a patient, improvement of symptoms and the like.

EXAMPLES

The present invention will be explained more specifically by referring to the following examples. However, the scope of the present invention is not limited to these examples. In the examples, the indications such as "Example A1" and "Example B1" correspond to the methods of preparation of the compounds embraced by the general formula (A1) and (B1), respectively. Compound numbers such as "Compound A1" and "Compound B1" correspond to the numbers of the compounds whose chemical structures are shown as particularly preferred compounds of the present invention.

Example A1

Synthesis of 5-(2'-benzimidazolylthio)pentyl bromide

2-Mercaptobenzimidazole (6.0 g) and 1,5-dibromopentane (60 g) were dissolved in ethanol (50 ml), and the solution was heated under reflux for six hours. After the solvent was evaporated under reduced pressure, the residue was added with ethyl acetate (50 ml) and hexane (50 ml) for digestion to obtain about 12 g of solid. Water (100 ml) was added to the solid, and the mixture was neutralized with aqueous sodium hydroxide. The deposited oil-soluble product was extracted with ethyl acetate, and the extract was concentrated after washing with water. The residue was applied to silica gel column chromatography (silica gel 220 g, solvent: chloroform) to obtain crude crystals (8.7 g). These crude crystals were recrystallized from ethanol to obtain the title compound (7.8 g).

Melting point: 126–127° C.

Elemental analysis: as $C_{12}H_{15}N_2SBr$

Calculated: C, 48.15; H, 5.05; N, 9.36 (%)

Found: C, 47.98; H, 5.11; N, 9.21 (%)

Example A2

Synthesis of 1-(2'-(5'-methylbenzimidazolyl)thio)-5-(2"-benzimidazolyl-thio)pentane (Compound A1)

5-(2'-Benzimidazolylthio)pentyl bromide (0.57 g) and 2-mercapto-5-methyl-benzimidazole (0.36 g) were dissolved in ethanol (5 ml), and the solution was heated under reflux for eight hours. After cooling, the reaction mixture was neutralized with aqueous sodium hydroxide, and the deposited oily product was extracted with ethyl acetate. After the extract was washed with water, the solvent was evaporated under reduced pressure, and the resulting oily product was separated and purified by silica gel column chromatography. The resulting crude product was crystallized from ethyl acetate to obtain the title compound (0.52 g).

Melting point: 163–165° C.
Elemental analysis: as $C_{20}H_{22}N_4S_2$
Calculated: C, 62.79; H, 5.80; N, 14.65 (%)
Found: C, 62.58; H, 5.71; N, 14.51 (%)

Example A3

Synthesis of 1-(2'-(5'-chlorobenzimidazolyl)thio)-5-(2"-benzimidazolyl-thio)pentane (Compound A2)

In the same manner as in Example A2, 0.61 g of the title compound was obtained (crystallized from ethyl acetate/acetonitrile) from 5-(2'-benzimidazolylthio)-pentyl bromide (0.6 g) and 5-chloro-2-mercaptobenzimidazole (0.37 g).

Melting point: 160–163° C.
Elemental analysis: as $C_{19}H_{19}N_4S_2Cl$
Calculated: C, 56.63; H, 4.75; N, 13.91 (%)
Found: C, 56.49; H, 4.60; N, 13.71 (%)

Example A4

Synthesis of 1-(2-(5'-chlorobenzimidazolyl)thio)-5-(2"-(5"-methylbenz-imidazolyl)thio)pentane (Compound A3)

In the same manner as in Example A1, 5-(2-(5'-methylbenzimidazolyl)-thio)pentyl bromide was synthesized from 2-mercapto-5-methylbenzimidazole and 1,5-dibromopentane. In the same manner as in Example A3, 0.6 g of the title compound was obtained (crystallized from ethanol/actonitrile) from the resulting 5-(2-(5'-methylbenzimidazolyl)thio)pentyl bromide (0.63 g) and 5-chloro-2-mercapto-benzimidazole (0.37 g).

Melting point: 174–175° C.
Elemental analysis: as $C_{20}H_{21}N_4S_2Cl$
Calculated: C, 57.60; H, 5.08; N, 13.44 (%)
Found: C, 57.44; H, 5.14; N, 13.58 (%)

Example A5

Synthesis of 1-(2'-(5'-methoxybenzimidazolyl)thio)-5-(2"-(5"-methylbenz-imidazolyl)thio)pentane (Compound A4)

In the same manner as in Example A4, 0.7 g of the title compound was obtained (crystallized from ethyl acetate) from 5-(2'-(5'-methylbenzimidazolyl)thio)-pentyl bromide (0.63 g) and 2-mercapto-5-methoxybenzimidazole (0.36 g).

Melting point: 170–171° C.
Elemental analysis: as $C_{21}H_{24}N_4OS_2$
Calculated: C, 61.13; H, 5.86; N, 13.58 (%)
Found: C, 60.98; H, 5.74; N, 13.42 (%)

Example A6

Synthesis of 1-(2'-benzimidazolylthio)-5-(2"-(5"-methoxybenzimidazolyl)-thio)pentane (Compound A5)

In the same manner as in Example A2, 0.89 g of the title compound (wax-like material) was obtained from 5-(2'-benzimidazolylthio)pentyl bromide (0.9 g) and 2-mercapto-5-methoxybenzimidazole (0.57 g).

Example A7

Synthesis of 1-(2'-benzimidazolylthio)-5-(2"-(5"-hydroxybenzimidazolyl)-thio)pentane (Compound A6)

Compound A5 (0.34 g) was dissolved in hydrobromic acid (2 ml) and water (2 ml), and the solution was heated under reflux for 16 hours. The reaction mixture was neutralized with aqueous sodium hydroxide, and then extracted with ethyl acetate. The extract was washed with water, and the solvent was evaporated under reduced pressure. The residue was crystallized from ethanol/ethyl acetate to obtain the title compound (0.18 g).

Melting point: 112–114° C.
Elemental analysis: as $C_{19}H_{20}N_4OS_2$
Calculated: C, 59.35; H, 5.24; N, 14.57 (%)
Found: C, 59.21; H, 5.12; N, 14.39 (%)

Example A8

Synthesis of 1-(2'-benzimidazolylthio)-5-(2"-(5"-methanesulfonylamino-benzimidazolyl)thio)pentane (Compound A7)

In the same manner as in Example A2, 0.32 g of the title compound was obtained (crystallized from ethyl acetate/acetonitrile) from 5-(2'-benzimidazolylthio)-pentyl bromide (0.3 g) and 2-mercapto-5-methanesulfonylaminobenzimidazole (0.28 g).

Melting point: 141–143° C.
Elemental analysis: as $C_{20}H_{23}N_5O_2S_3$
Calculated: C, 52.03; H, 5.02; N, 15.18 (%)
Found: C, 51.84; H, 4.98; N, 15.09 (%)

Example A9

Synthesis of 1-(2'-benzimidazolylthio)-5-(2"-(5"-propionylaminobenz-imidazolyl)thio)pentane (Compound A8)

In the same manner as in Example A2, 0.23 g of the title compound (wax-like product) was obtained from 5-(2'-benzimidazolylthio)pentyl bromide (0.3 g) and 2-mercapto-5-methanesulfonylaminobenzimidazole (0.22 g).

Example A10

Synthesis of 1-(2'-(5'-ethoxycarbonylbenzimidazolyl)thio)-5-(2"-benzimidazolylthio)pentane (Compound A9)

In the same manner as in Example A2, 0.14 g of the title compound was obtained (crystallized from ethyl acetate/acetonitrile) from 5-(2'-benzimidazolylthio)-pentyl bromide (0.3 g) and 2-mercapto-5-ethoxycarbonylbenzimidazole (0.22 g).

Melting point: 155–156° C.
Elemental analysis: as $C_{22}H_{24}N_4O_2S_2$
Calculated: C, 59.97; H, 5.49; N, 12.72 (%)
Found: C, 59.73; H, 5.38; N, 12.58 (%)

Example A11

Synthesis of 1-(2'-(5',6'-dimethylbenzimidazolyl)thio)-5-(2"-benz-imidazolylthio)pentane (Compound A10)

In the same manner as in Example A2, 0.54 g of the title compound was obtained (crystallized from ethyl acetate/ acetonitrile) from 5-(2'-benzimidazolylthio)-pentyl bromide (0.6 g) and 2-mercapto-5,6-dimethylbenzimidazole (0.35 g).

Melting point: 150–153° C.

Elemental analysis: as $C_{21}H_{24}N_4S_2$

Calculated: C, 63.60; H, 6.10; N, 14.13 (%)

Found: C, 63.36; H, 6.02; N, 14.32 (%)

Example A12

Synthesis of 1-(2'-(5',6'-dichlorobenzimidazolyl) thio)-5-(2"-benz-imidazolylthio)pentane (Compound A11)

In the same manner as in Example A2, 0.72 g of the title compound was obtained (crystallized from acetonitrile) from 5-(2'-benzimidazolylthio)pentyl bromide (0.6 g) and 5,6-dichloro-2-mercaptobenzimidazole (0.44 g).

Melting point: 167–169° C.

Elemental analysis: as $C_{19}H_{18}N_4S_2Cl_2$

Calculated: C, 52.17; H, 4.15; N, 12.81 (%)

Found: C, 52.03; H, 4.01; N, 12.62 (%)

Example A13

Synthesis of 6-(2'-benzimidazolylthio)hexyl bromide

In the same manner as in Example A1, 5.0 g of the title compound was obtained (crystallized from ethyl acetate/hexane) from 2-mercaptobenzimidazole (3.0 g) and 1,6-dibromohexane (24.4 g).

Example A14

Synthesis of 1-(2'-(5',6'-dichlorobenzimidazolyl) thio)-6-(2"-benz-imidazolylthio)hexane (Compound A12)

In the same manner as in Example A2, 0.39 g of the title compound was obtained (crystallized from ethyl acetate/chloroform) from 6-(2'-benzimidazolyl-thio)hexyl bromide (0.31 g) and 5,6-dichloro-2-mercaptobenzimidazole (0.22 g).

Melting point: 287–230° C.

Elemental analysis: as $C_{20}H_{20}N_4S_2Cl_2$

Calculated: C, 53.21; H, 4.47; N, 12.41 (%)

Found: C, 53.07; H, 4.22; N, 12.12 (%)

Example A15

Synthesis of 8-(2'-benzimidazolylthio)octyl bromide

In the same manner as in Example A1, 2.6 g of the title compound was obtained (crystallized from ethyl acetate/hexane) from 2-mercaptobenzimidazole (1.5 g) and 1,8-dibromooctane (13.6 g).

Example A16

Synthesis of 1-(2'-(5',6'-dichlorobenzimidazolyl) thio)-8-(2"-benz-imidazolylthio)octane (Compound A13)

In the same manner as in Example A2, 0.36 g of the title compound was obtained (crystallized from ethanol/water) from 8-(2'-benzimidazolylthio)octyl bromide (0.37 g) and 5,6-dichloro-2-mercaptobenzimidazole (0.22 g).

Melting point: 176–178° C.

Elemental analysis: as $C_{22}H_{24}N_4S_2Cl_2$

Calculated: C, 55.11; H, 5.05; N, 11.69 (%)

Found: C, 54.98; H, 4.88; N, 11.43 (%)

Example A17

Synthesis of 1-(2'-(5',6'-dichlorobenzimidazolyl) thio)-5-(2"-(5"-methyl-benzimidazolyl)thio)pentane (Compound A14)

In the same manner as in Example A2, 0.32 g of the title compound was obtained (crystallized from acetonitrile) from 5-(2'-(5'-methylbenzimidazolyl)thio)-pentyl bromide (0.32 g) and 5,6-dichloro-2-mercaptobenzimidazole (0.24 g).

Melting point: 161–165° C.

Elemental analysis: as $C_{20}H_{20}N_4S_2Cl_2$

Calculated: C, 53.21; H, 4.47; N, 12.41 ( %)

Found: C, 53.10; H, 4.29; N, 12.21 (%)

Example A18

Synthesis of 1-(2'-(5',6'-dichlorobenzimidazolyl) thio)-5-(2"-(5",6"-dimethylbenzimidazolyl)thio) pentane (Compound A 15)

In the same manner as in Example A1, 5-(2'-(5',6'-dimethylbenzimidazolyl)-thio)pentyl bromide (6.6 g) was obtained from 2-mercapto-5,6-dimethylbenzimidazole (5.34 g) and 1, 5-dibromopentane (34.5 g). Furthermore, in the same manner as in Example A2, 0.72 g of the title compound was obtained (crystallized from acetonitrile) from 5-(2'-(5', 6'-dimethylbenzimidazolyl)thio)pentyl bromide (0.65 g) and 5,6-dichloro-2-mercaptobenzimidazole (0.44 g).

Melting point: 171–173° C.

Elemental analysis: as $C_{21}H_{22}N_4S_2Cl_2$

Calculated: C, 54.19; H, 4.76; N, 12.04 (%)

Found: C, 54.03; H, 4.57; N, 12.11 (%)

Example A19

Synthesis of 1-(2'-(5'-chloro-6'-trifluoromethylbenzimidazolyl)thio) -5-(2"-benzimidazolylthio)pentane (Compound A16)

In the same manner as in Example A2, 0.29 g of the title compound (wax-like material) was obtained from 5-(2'-benzimidazolylthio)pentyl bromide (0.3 g) and 5-chloro-2-mercapto-6-trifluoromethylbenzimidazole (0.26 g).

Example A20

Synthesis of 1-(2'-(5'-cyanobenzimidazolyl)thio)-5-(2"-benzimidazolyl-thio)pentane (Compound A17)

In the same manner as in Example A2, 0.22 g of the title compound was obtained (crystallized from ethyl acetate/acetonitrile) from 5-(2'-benzimidazolyl-thio)pentyl bromide (0.3 g) and 5-cyano-2-mercaptobenzimidazole (0.16 g).

Melting point: 152–154° C.

Elemental analysis: as $C_{20}H_{19}N_5S_2$

Calculated: C, 61.04; H, 5.22; N, 17.80 (%)

Found: C, 59.96; H, 5.10; N, 17.64 (%)

Example A21

Synthesis of 4-(2'-benzimidazolylthio)butyl chloride

In the same manner as in Example A1, 6 g of the title compound (wax-like material) was obtained from 2-mercaptobenzimidazole (6.2 g) and 1,4-chlorobromo-butane (10.3 g).

Example A22

Synthesis of 1-(2'-(5'-methylbenzimidazolyl)thio)-4-(2"-benzimidazolyl-thio)butane (Compound A18)

In the same manner as in Example A2, 0.09 g of the title compound was obtained (crystallized from methanol/water) from 4-(2'-benzimidazolylthio)butyl chloride (0.33 g) and 5-methyl-2-mercaptobenzimidazole (0.24 g).

Melting point: 204–206° C.
Elemental analysis: as $C_{19}H_{20}N_4S_2$
Calculated: C, 61.92; H, 5.47; N, 15.21 (%)
Found: C, 61.78; H, 5.34; N, 15.10 (%)

Example A23

Synthesis of 1-(2'-(5'-methylbenzimidazolyl)thio)-6-(2"-benzimidazolyl-thio)hexane (Compound A19)

In the same manner as in Example A2, 0.33 g of the title compound was obtained (crystallized from ethyl acetate) from 6-(2'-benzimidazolylthio)hexyl bromide (0.31 g) and 5-methyl-2-mercaptobenzimidazole (0.16 g).

Melting point: 202–204° C.
Elemental analysis: as $C_{21}H_{24}N_4S_2$
Calculated: C, 63.60; H, 6.16; N, 14.13 (%)
Found: C, 63.42; H, 6.09; N, 14.01 (%)

Example A24

Synthesis of 1-(2'-(5'-methylbenzimidazolyl)thio)-8-(2"-benzimidazolyl-thio)octane (Compound A20)

In the same manner as in Example A2, 0.36 g of the title compound was obtained (crystallized from ethyl acetate/hexane) from 8-(2'-benzimidazolylthio)octyl bromide (0.37 g) and 5-methyl-2-mercaptobenzimidazole (0.16 g).

Melting point: 101–103° C.
Elemental analysis: as $C_{23}H_{28}N_4S_2$
Calculated: C, 65.05; H, 6.65; N, 13.20 (%)
Found: C, 64.87; H, 6.41; N, 13.34 (%)

Example A25

Synthesis of 2-(2-(2-p-toluenesulfonyloxy)ethoxy)ethylmercaptobenz-imidazole

2-Mercaptobenzimidazole (3.1 g) and diethylene glycol di-p-tosylate (8.3 g) were heated under reflux in acetonitrile for 18 hours. After the solvent was evaporated under reduced pressure, 2.4 g of the title compound (wax-like material) was separated from the residue by silica gel column chromatography.

Example A26

Synthesis of 2-(2-(2-(2'-(5'-methylbenzimidazolyl)thio)ethoxy)ethyl-mercaptobenzimidazole (Compound A21)

In the same manner as in Example A1, 0.21 g of the title compound was obtained from 2-(2-(2-p-toluenesulfonyloxy)ethoxy)ethylmercaptobenzimidazole (0.38 g) and 2-mercapto-5-methylbenzimidazole (0.17 g)

Melting point: 130–131° C.

Elemental analysis: as $C_{19}H_{20}N_4OS_2$
Calculated: C, 59.35; H, 4.96; N, 14.57 (%)
Found: C, 59.12; H, 4.72; N, 14.32 (%)

Example A27

Synthesis of 2-(2-(2-(2-p-toluenesulfonyloxy)ethoxy)ethoxy)ethyl-mercaptobenzimidazole 2-Mercaptobenzimidazole (3.1 g) and triethylene glycol di-p-tosylate (9.6 g) were heated under reflux in acetonitrile for 18 hours. The solvent was evaporated under reduced pressure, and 3.3 g of the title compound (wax-like material) was separated from the residue by silica gel column chromatography.

Example A28

Synthesis of 2-(2-(2-(2-(2'-(5'-methylbenzimidazolyl)thio)ethoxy)-ethoxy)ethylmercaptobenzimidazole (Compound A22)

In the same manner as in Example A1, 0.33 g of the title compound was obtained from 2-(2-(2-(2-p-toluenesulfonyloxy)ethoxy)ethoxy)ethylmercaptobenzimidazole (0.43 g) and 2-mercapto-5-methylbenzimidazole (0.17 g)

Melting point: 119–122° C.
Elemental analysis: as $C_{21}H_{24}N_4O_2S_2$
Calculated: C, 58.85; H, 5.64; N, 13.08 (%)
Found: C, 58.59; H, 5.45; N, 12.89 (%)

Example A29

Synthesis of 1-(2'-(1'-methyl-5'-methylsulfamoylbenzimidazolyl)thio)-5-(2"-benzimidazolylthio)pentane (Compound A23)

In the same manner as in Example A2, 0.22 g of the title compound was obtained (crystallized from ethyl acetate/acetonitrile) from 5-(2'-benzimidazolyl-thio)pentyl bromide (0.3 g) and 2-mercapto-1-methyl-5-methylsulfamoylbenzimidazole (0.26 g).

Melting point: 139–140° C.
Elemental analysis: as $C_{21}H_{25}N_5O_2S_3$
Calculated: C, 53.03; H, 5.30; N, 14.73 (%)
Found: C, 52.92; H, 5.13; N, 14.61 (%)

Example A30

Synthesis of 1-(2'-(1'-methyl-5'-methylsulfamoylbenzimidazolyl)thio)-5-(2"-(1-propionyl)benzimidazolyl)thio)pentane (Compound A25)

1-(2'-(1'-Methyl-5'-methylsulfamoylbenzimidazolyl) thio)-5-(2"-benzimidazolyl-thio)pentane (0.1 g) was dissolved in a mixture of dimethylacetamide (0.3 ml), acetonitrile (0.5 ml) and triethylamine (0.1 ml), and the mixture was slowly added with propionyl chloride (4 ml) at 45° C. After stirring was continued for 4.5 hours, the mixture was added with water and then extracted with ethyl acetate. The solvent was evaporated under reduced pressure, and the residue was purified by silica gel column chromatography, and then crystallized from ethyl acetate/acetonitrile to obtain 0.04 g of the title compound.

Melting point: 91–93° C.
Elemental analysis: as $C_{24}H_{29}N_5O_3S_3$

Calculated: C, 54.21; H, 5.50; N, 13.17 (%)
Found: C, 54.11; H, 5.32; N, 13.02 (%)

Example A31

Synthesis of ethyl 6-(2-benzimidazolylthio)caproate

2-Mercaptobenzimidazole (6.3 g) and 6-bromocaproic acid (7.8 g) were dissolved in ethanol (35 ml), and the solution ws heated under reflux for 12 hours. After cooling, the reaction was added with water, and the mixture was adjusted to pH 8 with aqueous sodium carbonate. The deposited crystals were collected by filtration, and dried to obtain 11.2 g of the title compound.

Example A32

Synthesis of 2-(5-(2'-benzimidazolylthio)pentyl) benzimidazole (Compound A27)

Ethyl 6-(2-benzimidazolylthio)caproate (0.88 g) and o-phenylenediamine (0.34 g) were dissolved in concentrated hydrochloric acid (1 ml) and water (2 ml), and the mixture was heated under reflux under nitrogen flow for 20 hours. After cooling, the reaction mixture was added with water (3 ml), and the precipitates were collected by filtration. The precipitates were suspended in water/methanol (1:1), and aqueous sodium hydroxide was added to the suspension so as to be maintained at pH 8. The deposited crystals were collected by filtration and washed with water-containing methanol until they became neutral to obtain 0.88 g of the title compound.

Melting point: 313–316° C.
Elemental analysis: as $C_{19}H_{20}N_4S$
Calculated: C, 67.82; H, 5.99; N, 16.66 (%)
Found: C, 67.65; H, 5.72; N, 16.52 (%)

Example A33

Synthesis of 1-propionyl-2-(5-(2'-(1-propionylbenzimidazolyl)thio)-pentyl)benzimidazole (Compound A24)

In the same manner as in Example A30, 0.17 g of the title compound was obtained from 2-(5-(2'-benzimidazolylthio) pentyl)benzimidazole (0.2 g).

Melting point: 142–145° C.
Elemental analysis: as $C_{25}H_{28}N_4O_2S$
Calculated: C, 66.93; H, 6.29; N, 12.49 (%)
Found: C, 66.76; H, 6.11; N, 12.22 (%)

Example A34

Synthesis of 1-methyl-2-(5-(2'-(1-methylbenzimidazolyl)thio)pentyl)-benzimidazole (Compound A26)

2-(5-(2'-Benzimidazolylthio)pentyl)benzimidazole (0.2 g) was dissolved in dimethylformamide (2 ml), and the solution was added with potassium carbonate (0.18 g) and methyl iodide (0.3 g), and then the mixture was stirred at 40° C. for 14 hours. After cooling, the reaction was added with water, and then extracted with ethyl acetate. After the extract was washed with water, the solvent was evaporated under reduced pressure, and the residue was crystallized from ethyl acetonitrile to obtain 0.03 g of the title compound.

Melting point: 118–120° C.
Elemental analysis: as $C_{21}H_{24}N_4S$
Calculated: C, 69.19; H, 6.64; N, 15.31 (%)
Found: C, 69.03; H, 6.41; N, 15.23 (%)

Example A35

Synthesis of 2-(5-(2'-benzimidazolylthio)pentyl)-5, 6-dimethylbenz-imidazole (Compound A28)

In the same manner as in Example A32, 0.70 g of the title compound was obtained (crystallized from ethyl acetate/acetonitrile) from ethyl 6-(2-benzimidazolyl-thio)caproate (0.88 g) and 4,5-dimethyl-o-phenylenediamine (0.43 g).

Melting point: 211–214° C.
Elemental analysis: as $C_{21}H_{24}N_4S$
Calculated: C, 69.19; H, 6.64; N, 15.31 (%)
Found: C, 69.11; H, 6.48; N, 15.12 (%)

Example A36

Synthesis of 2-(5-(2'-benzimidazolylthio)pentyl)-5, 6-dichlorobenz-imidazole (Compound A28)

In the same manner as in Example A32, 0.93 g of the title compound was obtained (crystallized from ethyl acetate/acetonitrile) from ethyl 6-(2-benzimidazolyl-thio)caproate (0.88 g) and 4,5-dichloro-o-phenylenediamine (0.56 g).

Melting point: 194–196° C.
Elemental analysis: as $C_{19}H_{18}N_4SCl_2$
Calculated: C, 56.30; H, 4.48; N, 13.83 (%)
Found: C, 56.24; H, 4.37; N, 13.69 (%)

Example A37

Synthesis of 2-(5-(2'-benzimidazolylthio)pentyl)-5-nitrobenzimidazole (Compound A29)

In the same manner as in Example A32, 0.50 g of the title compound was obtained (crystallized from ethyl acetate/acetonitrile) from ethyl 6-(2-benzimidazolyl-thio)caproate (0.88 g) and 4-nitro-o-phenylenediamine (0.48 g).

Melting point: 184–185° C.
Elemental analysis: as $C_{19}H_{19}N_5O_2S$
Calculated: C, 59.82; H, 5.02; N, 18.36 (%)
Found: C, 59.59; H, 4.98; N, 18.44 (%)

Example A38

Synthesis of 2-(7-(2'-benzimidazolylthio)heptyl) benzimidazole (Compound A31)

In the same manner as in Example A31, 6.4 g of ethyl 8-(2-benzimidazolyl-thio)octanoate was obtained from 2-mercaptobenzimidazole (3.1 g) and 8-bromooctanoic acid (4.46 g). Then, in the same manner as in Example A32, 0.70 g of the title compound was obtained from ethyl 8-(2-benzimidazolylthio)octanoate (0.96 g) and o-phenylenediamine (0.34 g).

Melting point: 263–264° C.
Elemental analysis: $C_{21}H_{24}N_4S$
Calculated: C, 69.19; H, 6.64; N, 15.37 (%)
Found: C, 69.03; H, 6.48; N, 15.21 (%)

Example A39

Synthesis of 2-(11-(2'-benzimidazolylthio)undecyl) benzimidazole (Compound A32)

In the same manner as in Example A31, 6.4 g of ethyl 12-(2-benzimidazolyl-thio)dodecanoate was obtained from 2-mercaptobenzimidazole (3.1 g) and 12-bromododecanoic acid (5.3 g). Then, in the same manner as in Example A32, 0.70 g of the title compound was obtained from ethyl 11-(2-benzimidazolylthio)dodecanoate (1.13 g) and o-phenylenediamine (0.34 g).

Melting point: 206–208° C.
Elemental analysis: as $C_{25}H_{32}N_4S$
Calculated: C, 71.39; H, 7.67; N, 13.32 (%)
Found: C, 71.22; H, 7.41; N, 13.19 (%)

Example A40

Synthesis of 1-(2'-benzimidazolylthio)-5-(2"-benzothiazolylthio)pentane (Compound A33)

In the same manner as in Example A2, 0.2 g of the title compound was obtained (crystallized from acetonitrile) from 5-(2'-benzimidazolylthio)pentyl bromide (0.3 g) and 2-mercaptobenzothiazole (0.17 g).

Melting point: 124–125° C.
Elemental analysis: as $C_{19}H_{19}N_3S_3$
Calculated: C, 59.19; H, 4.97; N, 10.90 (%)
Found: C, 59.31; H, 4.75; N, 10.70 (%)
Compound A36 was also synthesized in a similar manner.

Example A41

Synthesis of 1-(2'-benzimidazolylthio)-5-(2"-(5"-chlorobenzothiazolyl)-thio)pentane (Compound A34)

In the same manner as in Example A2, 0.38 g of the title compound was obtained (crystallized from acetonitrile) from 5-(2'-benzimidazolylthio)pentyl bromide (0.3 g) and 5-chloro-2-mercaptobenzothiazole (0.20 g).

Melting point: 125–127° C.
Elemental analysis: as $C_{19}H_{18}N_3S_3Cl$
Calculated: C, 54.33; H, 4.32; N, 10.01 (%)
Found: C, 54.11; H, 4.12; N, 10.12 (%)

Example A42

Synthesis of 1-(2'-benzimidazolylthio)-5-(2"-(6"-ethoxy benzothiazolyl)-thio)pentane (Compound A35)

In the same manner as in Example A2, 0.38 g of the title compound was obtained (crystallized from acetonitrile) from 5-(2'-benzimidazolylthio)pentyl bromide (0.3 g) and 6-ethoxy-2-mercaptobenzothiazole (0.21 g).

Melting point: 122–124° C.
Elemental analysis: as $C_{21}H_{23}N_3OS_3$
Calculated: C, 58.71; H, 5.40; N, 9.78 (%)
Found: C, 58.54; H, 5.32; N, 9.65 (%)

Example A43

Synthesis of 1-(2'-benzimidazolylthio)-5-(2"-benzoxazolylthio)pentane (Compound A37)

In the same manner as in Example A2, 0.1 g of the title compound was obtained (crystallized from acetonitrile) from 5-(2'-benzimidazolylthio)pentyl bromide (0.3 g) and 2-mercaptobenzoxazole (0.15 g).

Melting point: 128–130° C.
Elemental analysis: as $C_{19}H_{19}N_3OS_2$
Calculated: C, 61.76; H, 5.18; N, 11.38 (%)
Found: C, 61.49; H, 5.02; N, 11.21 (%)
Compound A38 was also synthesized in a similar manner.

Example A44

Synthesis of 1-(2'-benzimidazolylthio)-5-(2"-(5"-phenylbenzoxazolyl)-thio)pentane (Compound A39)

In the same manner as in Example A2, 0.2 g of the title compound was obtained (crystallized from ethyl acetate/acetonitrile) from 5-(2'-benzimidazolylthio)-pentyl bromide (0.3 g) and 2-mercapto-5-phenylbenzoxazole (0.23 g).

Melting point: 100–102° C.
Elemental analysis: as $C_{25}H_{23}N_3OS_2$
Calculated: C, 67.38; H, 5.20; N, 9.43 (%)
Found: C, 67.45; H, 5.08; N, 9.23 (%)

Example B1

Synthesis of 1-(2'-benzimidazolylthio)-5-(2"-imidazolylthio)pentane (Compound B1)

5-(2'-Benzimidazolylthio)pentyl bromide (0.30 g) and 2-mercaptoimidazole (0.10 g) were dissolved in ethanol (3 ml), and the resulting solution was added with triethylamine (0.16 ml), and then the mixture was heated under reflux for 7 hours. After cooling, the reaction mixture was neutralized with aqueous sodium hydroxide, and the deposited oily product was extracted with ethyl acetate. The extract was washed with water, and then the solvent was evaporated under reduced pressure. The residue was then crystallized from acetonitrile to obtain 0.23 g of the title compound.

Melting point: 101–104° C.
Elemental analysis: as $C_{15}H_{18}N_4S_2$
Calculated: C, 56.57; H, 5.70; N, 17.60 (%)
Found: C, 56.43; H, 5.61; N, 17.66 (%)

Example B2

In the same manner as in Example B1, compounds mentioned in the following Table 1 were synthesized.

TABLE 1

| Compound No. | Melting point (° C.) |
|---|---|
| Compound B2 | 57–58 |
| Compound B4 | 133–135 |
| Compound B5 | 150–152 |
| Compound B6 | 82–83 |
| Compound B7 | 100–102 |
| Compound B8 | 108–110 |
| Compound B9 | 130–133 |
| Compound B10 | 119–120 |
| Compound B11 | 48–49 |
| Compound B12 | 84–85 |
| Compound B13 | 148–149 |
| Compound B14 | 254–256 |
| Compound B15 | 89–91 |
| Compound B16 | 82–83 |
| Compound B17 | 182–183 |
| Compound B18 | 79–81 |
| Compound B19 | 96–98 |
| Compound B20 | 89–91 |
| Compound B22 | 127–128 |
| Compound B24 | 132–134 |
| Compound B25 | 76–77 |
| Compound B26 | 141–143 |
| Compound B27 | 122–124 |
| Compound B29 | 107–109 |

TABLE 1-continued

| Compound No. | Melting point (° C.) |
|---|---|
| Compound B30 | 98–101 |
| Compound B31 | 94–95 |
| Compound B32 | 102–103 |
| Compound B36 | 145–147 |
| Compound B37 | 121–123 |
| Compound B38 | 108–110 |
| Compound B39 | 149–152 |
| Compound B40 | 108–110 |
| Compound B41 | 79–80 |
| Compound B42 | 84–85 |
| Compound B49 | 102–103 |
| Compound B50 | 75–77 |
| Compound B51 | 88–89 |
| Compound B52 | 120–123 |
| Compound B53 | 125–127 |
| Compound B54 | 135–137 |
| Compound B56 | 102–104 |
| Compound B57 | 106–107 |
| Compound B58 | 170–172 |
| Compound B59 | 174–177 |
| Compound B60 | 166–168 |
| Compound B61 | 152–154 |
| Compound B62 | 130–132 |
| Compound B63 | 125–126 |
| Compound B66 | 129–131 |

Example B3

In the same manner as in Example B2, Compound B3, Compound B21, Compound B23, Compound B28, Compound B33, Compound B35, and Compound B55 were prepared. All of the compounds were obtained as oil. After the completion of reactions, reaction mixtures were neutralized with sodium carbonate, and extracted with ethyl acetate. The extracts were washed with water and concentrated, and then resulting residues were purified by silica gel column chromatography (developing solvent: ethyl acetate/chloroform).

Example B4

Synthesis of 5-(2'-pyridylthio)pentyl bromide hydrobromide

2-Mercaptopyridine (5.55 g) and 1,5-dibromopentane (68.7 g) were dissolved in ethanol (40 ml), and the solution was heated under reflux for 9 hours. After the solvent was evaporated under reduced pressure, the residue was digested with ethyl acetate (50 ml) and hexane (50 ml) to obtain about 12 g of the title compound as a solid product.

Example B5

Synthesis of 1-(2'-(5'-methoxybenzimidazolyl)-5-(2"-pyridylthio)pentane (Compound B34)

5-(2'-Pyridylthio)pentyl bromide hydrobromide (0.37 g) and 5-methoxy-2-mercaptobenzimidazole (0.58 g) were dissolved in ethanol (3 ml), and the solution was heated under reflux for 14 hours. After cooling, the reaction mixture was neutralized with aqueous sodium carbonate, and then extracted with ethyl acetate. The extract was washed with water, and the solvent was evaporated under reduced pressure. The residue was purified by silica gel column chromatography (developing solvent: ethyl acetate/chloroform) to obtain 0.3 g of the title compound as an oil.

Example B6

Synthesis of ethyl 6-(2-pyridylthio)caproate

2-Mercaptopyridine (5.84 g) and 6-bromocaproic acid (9.75 g) were dissolved in ethanol (50 ml), and the solution was heated under reflux for 14 hours. After cooling, the reaction mixture was added with water, and adjusted to pH 8 with aqueous sodium carbonate. The deposited oily product was extracted with ethyl acetate, and then purified by silica gel column chromatography (developing solvent: chloroform/ethyl acetate) to obtain 13.6 g of the title compound.

Example B7

Synthesis of 1-(2'-benzimidazolylthio)-5-(2"-pyridyl)pentane (Compound B43)

Ethyl 6-(2-pyridylthio)caproate (2.5 g) and o-phenylenediamine (1.1 g) were dissolved in concentrated hydrochloric acid (3.3 ml) and water (7 ml), and then the mixture was heated under reflux under nitrogen flow for 20 hours. After cooling, the reaction mixture was added with water, neutralized with sodium carbonate, and then extracted with ethyl acetate. The extract was washed with water and concentrated, and the residue was crystallized from ethyl acetate/acetonitrile to obtain 1.54 g of the title compound.

Melting point: 135–136° C.

Elemental analysis: as $C_{16}H_{19}N_3S_2$

Calculated: C, 67.33; H, 6.71; N, 14.73 (%)

Found: C, 67.25; H, 6.62; N, 14.59 (%)

Example B8

In the same manner as in Example B5 and Example B6, compounds listed in Table 2 below were synthesized. Compound B44 (as an oil) was also synthesized in a similar manner. For Compound B44, after the completion of the reaction, a reaction mixture was neutralized with sodium carbonate, and then extracted with ethyl acetate. The extract was washed with water and concentrated, and the resulting residue was purified by silica gel column chromatography (developing solvent: methanol/chloroform).

TABLE 2

| Compound No. | Melting point (° C.) |
|---|---|
| Compound B45 | 122–125 |
| Compound B46 | 112–114 |
| Compound B47 | 99–101 |
| Compound B48 | 88–90 |

Example B9

Synthesis of 5-(2'-(1'-methylbenzimidazolyl)thio)-1-(2"-pyridylthio)-pentane (Compound B64)

5-(2'-Benzimidazolylthio)-1-(2"-pyridylthio)pentane (Compound B30, 0.33 g) was dissolved in dimethylformamide (2.2 ml), and the solution was added with methyl iodide (0.17 g) and potassium carbonate (0.27 g), and the the mixture was stirred at 40° C. for three hours. The reaction mixture was poured into water, and then extracted with ethyl acetate. The extract was washed with water, and the solvent was evaporated under reduced pressure. The residue was purified by silica gel column chromatography (developing solvent: ethyl acetate/chloroform) to obtain 0.3 g of the title compound as oily product.

Example B10

Synthesis of 5-(2'-(1'-propionylbenzimidazolyl)thio)-1-(2"-pyridylthio)-pentane (Compound B65)

5-(2'-Benzimidazolylthio)-1-(2"-pyridylthio)pentane (Compound B30, 0.33 g) was dissolved in a mixture of dimethylacetamide (1.0 ml), acetonitrile (1.5 ml), and triethylamine (0.3 ml), and then the solution was added slowly with propionyl chloride (0.12 ml) at 50° C. After stirring was continued for three hours, the reaction mixture was poured into water and then extracted with ethyl acetate. The extract was washed with water, and the solvent was evaporated under reduced pressure. The residue was crystallized from water-containing acetonitrile to obtain 0.23 g of the title compound.

Melting point: 54–55° C.

Elemental analysis: as $C_{20}H_{23}N_3OS_2$

Calculated: C, 62.30; H, 6.01; N, 10.90 (%)

Found: C, 62.18; H, 5.92; N, 10.78 (%)

Example B11

Synthesis of 2-(2-(2-p-toluenesulfonyloxy)ethoxy)ethylmercaptobenz-imidazole

2-Mercaptobenzimidazole (3.1 g) and diethylene glycol di-p-tosylate (8.3 g) were heated under reflux in acetonitrile for 18 hours. After the solvent was evaporated under reduced pressure, the residue was purified by silica gel column chromatography to obtain 2.4 g of the title compound (wax-like product).

Example B12

Synthesis of 2-(2-(2-(2'-pyridylthio)ethoxy)ethylmercaptobenzimidazole (Compound B67)

In the same manner as in Example A1, 0.21 g of the title compound was obtained as oily product from 2-(2-(2-p-toluenesulfonyloxy)ethoxy)ethylmercapto-benzimidazole (0.27 g) and 2-mercaptopyridine (0.10 g). The oily product was purified by silica gel chromatography (ethyl acetate/chloroform).

Example B13

Synthesis of 2-(2-(2-(2-p-toluenesulfonyloxy)ethoxy)ethoxy)ethyl-mercaptobenzimidazole 2-Mercaptobenzimidazole (3.1 g) and triethylene glycol di-p-tosylate (9.6 g) were heated under reflux in acetonitrile for 18 hours. After the solvent was evaporated under reduced pressure, 3.3 g of the title compound (wax-like product) was separated from the residue by silica gel column chromatography.

Example B14

Synthesis of 2-(2-(2-(2-(2'-pyridylthio)ethoxy)ethoxy)ethylmercapto-benzimidazole (Compound B68)

In the same manner as in Example A1, 0.18 g of the title compound was obtained as oily product from 2-(2-(2-(2-p-toluenesulfonyloxy)ethoxy)ethoxy)-ethyl-mercaptobenzimidazole (0.31 g) and 2-mercaptopyridine (0.10 g). The oily product was purified by silica gel chromatography (developing solvent: ethyl acetate/chloroform).

Test Example 1

Activity of the Compounds of the Present Invention for Suppressing the Foaming of Macrophages Activity of the compounds of the present invention for suppressing the foaming of macrophages, which triggers arterial sclerosis, was examined by an in vitro experiment using mouse peritoneal macrophages. 15-Week old female ICR mice (Nippon SLC) were subjected to bleeding by cutting off their cervicalis, and Hanks buffer (Nippon Seiyaku) was injected into their peritoneal cavities. After abdominal regions of the mice were massaged, the buffer was recovered immediately, and then the resulting buffer was centrifuged at 1,000 r.p.m. for five minutes to collect peritoneal macrophages. Then, the collected macrophages were suspended in GTI medium (Wako Pure Chemical Industries), and inoculated onto a 24-well microtiter plate. After the macrophages were cultivated at 37° C. under 5% $CO_2$ for two hours, the culture medium was changed with Dulbecco Modified Eagle Medium (MEM, Nippon Seiyaku). The macrophages were further cultivated at 37° C. under 5% $CO_2$ for 16 hours, and then a test compound and liposomes were added to the culture.

1) Test compound: dissolved in DMSO (Wako Pure Chemical Industries),
2) Liposomes: PC/PS/DCP/CHOL=50/50/10/75 (nmol)

PC: Phosphatidylcholine (Funakoshi);

PS: Phosphatidylserine (Funakoshi);

DCP: Dicetylphosphate (Funakoshi);

CHOL: Cholesterol (Sigma)

After cultivation was further continued at 37° C. under 5% $CO_2$ for 16 hours, lipid fraction was extracted with chloroform and methanol. The extracted lipid fraction was dissolved in isopropyl alcohol, and the produced cholesterol ester (CE) was quantified by an enzymatic luminescence method. Yield of the cholesterol ester was calculated as a relative ratio based on yield of the control as 100% where no test compound was added. Cytotoxicity was examined microscopically by observing morphological alteration of cells. The results are shown in Table 3 and Table 4 set out below. In the tables, compound numbers correspond to those of the compounds of present invention described in the examples. The following compound was used as a control for the experiments using the compounds of B series.

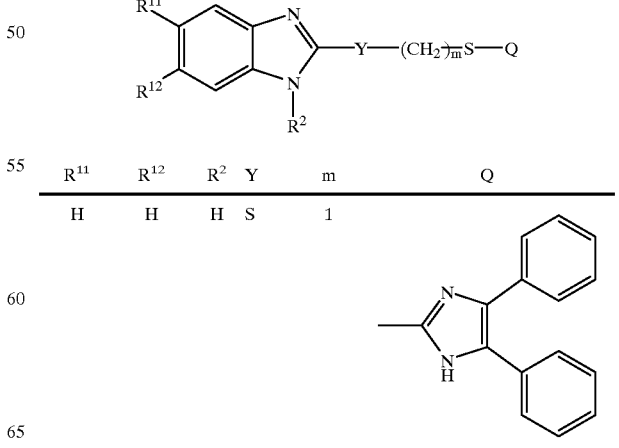

| $R^{11}$ | $R^{12}$ | $R^2$ | Y | m | Q |
|---|---|---|---|---|---|
| H | H | H | S | 1 | |

TABLE 3

| Compound | Dose (μM) | Rate of CE synthesis (%) | Cytotoxicity |
|---|---|---|---|
| A1  | 5 | 41 | Not observed |
| A2  | 5 | 52 | Not observed |
| A3  | 5 | 36 | Not observed |
| A4  | 5 | 41 | Not observed |
| A5  | 5 | 39 | Not observed |
| A6  | 5 | 46 | Not observed |
| A7  | 5 | 22 | Not observed |
| A8  | 5 | 24 | Not observed |
| A9  | 5 | 28 | Not observed |
| A10 | 5 | 20 | Not observed |
| A11 | 5 | 9  | Not observed |
| A12 | 5 | 42 | Not observed |
| A13 | 5 | 58 | Not observed |
| A14 | 5 | 42 | Not observed |
| A15 | 5 | 36 | Not observed |
| A16 | 5 | 34 | Not observed |
| A17 | 5 | 24 | Not observed |
| A18 | 5 | 52 | Not observed |
| A19 | 5 | 54 | Not observed |
| A20 | 5 | 61 | Not observed |
| A21 | 5 | 24 | Not observed |
| A22 | 5 | 20 | Not observed |
| A23 | 5 | 34 | Not observed |
| A24 | 5 | 40 | Not observed |
| A25 | 5 | 32 | Not observed |
| A26 | 5 | 35 | Not observed |
| A27 | 5 | 48 | Not observed |
| A28 | 5 | 49 | Not observed |
| A30 | 5 | 52 | Not observed |
| A31 | 5 | 53 | Not observed |
| A32 | 5 | 62 | Not observed |
| A33 | 5 | 13 | Not observed |
| A34 | 5 | 28 | Not observed |
| A35 | 5 | 25 | Not observed |
| A36 | 5 | 21 | Not observed |
| A37 | 5 | 13 | Not observed |
| A38 | 5 | 16 | Not observed |
| A39 | 5 | 24 | Not observed |

TABLE 4

| Compound | Dose (μM) | Rate of CE synthesis (%) | Cytotoxicity |
|---|---|---|---|
| B1  | 5 | 41  | Not observed |
| B2  | 5 | 16  | Not observed |
| B3  | 5 | 34  | Not observed |
| B4  | 5 | 47  | Not observed |
| B5  | 5 | 14  | Not observed |
| B6  | 5 | 22  | Not observed |
| B7  | 5 | 21  | Not observed |
| B8  | 5 | 24  | Not observed |
| B9  | 5 | 35  | Not observed |
| B10 | 5 | 32  | Not observed |
| B11 | 5 | 18  | Not observed |
| B12 | 5 | 14  | Not observed |
| B13 | 5 | 26  | Not observed |
| B14 | 5 | 48  | Not observed |
| B15 | 5 | 11  | Not observed |
| B16 | 5 | 9.3 | Not observed |
| B17 | 5 | 18  | Not observed |
| B18 | 5 | 35  | Not observed |
| B19 | 5 | 21  | Not observed |
| B20 | 5 | 24  | Not observed |
| B21 | 5 | 11  | Not observed |
| B22 | 5 | 21  | Not observed |
| B23 | 5 | 38  | Not observed |
| B24 | 5 | 9.5 | Not observed |
| B25 | 5 | 41  | Not observed |
| B26 | 5 | 12  | Not observed |
| B27 | 5 | 15  | Not observed |
| B28 | 5 | 7.6 | Not observed |
| B29 | 5 | 14  | Not observed |
| B30 | 5 | 9.0 | Not observed |
| B31 | 5 | 27  | Not observed |
| B32 | 5 | 37  | Not observed |
| B33 | 5 | 18  | Not observed |
| B34 | 5 | 37  | Not observed |
| B35 | 5 | 46  | Not observed |
| B36 | 5 | 26  | Not observed |
| B37 | 5 | 20  | Not observed |
| B38 | 5 | 22  | Not observed |
| B39 | 5 | 28  | Not observed |
| B40 | 5 | 25  | Not observed |
| B41 | 5 | 19  | Not observed |
| B42 | 5 | 12  | Not observed |
| B43 | 5 | 12  | Not observed |
| B44 | 5 | 51  | Not observed |
| B45 | 5 | 48  | Not observed |
| B46 | 5 | 36  | Not observed |
| B47 | 5 | 23  | Not observed |
| B48 | 5 | 41  | Not observed |
| A49 | 5 | 11  | Not observed |
| B50 | 5 | 22  | Not observed |
| B51 | 5 | 24  | Not observed |
| B52 | 5 | 49  | Not observed |
| B53 | 5 | 52  | Not observed |
| B54 | 5 | 24  | Not observed |
| B55 | 5 | 52  | Not observed |
| B56 | 5 | 18  | Not observed |
| B57 | 5 | 26  | Not observed |
| B58 | 5 | 18  | Not observed |
| B59 | 5 | 9.2 | Not observed |
| B60 | 5 | 14  | Not observed |
| B61 | 5 | 12  | Not observed |
| B62 | 5 | 25  | Not observed |
| B63 | 5 | 15  | Not observed |
| B64 | 5 | 24  | Not observed |
| B65 | 5 | 22  | Not observed |
| B66 | 5 | 52  | Not observed |
| B67 | 5 | 54  | Not observed |
| Control compound | 5 | 102 | Not observed |

The above results clearly demonstrate that the compounds of the present invention remarkably reduced the rate of cholesterol ester synthesis without cytotoxicity against macrophages, and that they can suppress the foaming of macrophages, which directly triggers the onset of arterial sclerosis. In the above tables, a smaller value means a more potent suppression, and 100% indicates no suppression. On the other hand, the diphenylimidazole derivative used as a control did not exhibit activity for suppressing the foaming of macrophages.

Test Example 2

Activity of the Compounds of the Present Invention for Suppressing the Formation of Arterial Sclerosis Lesions (in vivo experiment)

By using rabbits fed with high cholesterol food, effect on lipid in blood and activity of the compounds of the present invention for suppressing formation of arterial sclerosis lesions were examined. Hypercholesterolemia condition was created by feeding NZW rabbits (male) weighing about 2 kg with high cholesterol feed (100 g/day/rabbit of OCR-4 [Oriental Yeast]+0.5% cholesterol+0.5% olive oil) for seven days. A group consisting of three rabbits was continuously administered with a compound of the present invention (Compound B16 or Compound B49) for seven days by mixing the compound with the above feed at an amount of 100 mg/kg/day/rabbit. Another group consisting of three rabbits was fed solely with the high cholesterol feed and used as a control group.

Blood was collected from parotid veins with one week interval, and total cholesterol, LDL cholesterol, HDL cholesterol, GOT, and GPT were measured. In the groups administered with the compounds of the present invention, LDL cholesterol was reduced by 35% in the group administered with Compound B16, and reduced by 30% in the group administered with Compound B49 compared with the control group, although no difference in total cholesterol was observed. On the other hand, increase of HDL cholesterol by 30% was observed in each of the groups administered with the compounds of the present invention. No abnormal value was observed for GOT and GPT during the experiment.

Aortas were removed seven weeks after the administration, and cholesterol deposited on inner vascular walls was quantified. In the groups administered with Compound B16 or Compound B49, the amount of deposited cholesterol was reduced by 40% and 45% compared with control, respectively. These results clearly demonstrate that the compounds of the present invention have low toxicity, and have excellent activities for reducing LDL cholesterol, increasing HDL cholesterol, and suppressing the formation of arterial sclerosis lesions.

Industrial Applicability

The compounds of the present invention are useful as an active ingredient of preventive and/or therapeutic medicament of hyperlipemia, and preventive and/or therapeutic medicament of arterial sclerosis.

What is claimed is:

1. A benzimidazole compound represented by the following formula:

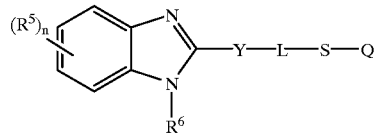

wherein, Y represents a single bond or sulfur atom:

$R^5$ represents hydrogen atom, a halogen atom, an alkyl group, a haloalkyl group, an aryl group, an alkoxy group, an aryloxy group, an alkoxycarbonyl group, an unsubstituted or substituted carbamoyl group, an unsubstituted or substituted sulfamoyl group, an acylamino group, an unsubstituted or substituted sulfonylamino group, cyano group, hydroxyl group, or nitro group;

$R^6$ represents hydrogen atom, an alkyl group, an acyl group, a sulfonyl group, an alkoxycarbonyl group, a sulfamoyl group, or a carbamoyl group;

n represents an integer of 1, 2 or 3, and when n represents 2 or 3, $R^5$ may be the same or different substituted on the benzene ring, respectively;

L represents a linking group selected from a group consisting of a $C_{2-12}$ alkylene group, and an alkylene group containing one or more phenylene groups or ether groups and having 4–12 atoms that constitute a full length of a linking chain; and Q represents a substituted or unsubstituted 1,3,4-oxadiazole ring or 1,2,4-oxadiazole ring.

2. The compound according to claim 1, wherein Y represents a single bond or sulfur atom; $R^5$ represents hydrogen atom, a halogen atom, an alkyl group, an alkoxy group, an alkoxycarbonyl group, a carbamoyl group, a sulfamoyl group, an acylamino group, a sulfonylamino group, or nitro group; $R^6$ represents hydrogen atom, an alkyl group, or an acyl group; n represents 1 or 2; and L represents a linking group selected from a $C_{4-11}$ alkylene group or an alkylene group containing one or more ether groups and having 5–8 atoms constituting a full length of a linking chain.

3. The compound according to claim 1, wherein Y represents a single bond or sulfur atom; $R^5$ represents hydrogen atom, a halogen atom, a $C_{1-4}$ alkyl group, a $C_{1-4}$ alkoxy group, a $C_{1-4}$ alkoxycarbonyl group, a substituted or unsubstituted carbamoyl group, a substituted or unsubstituted sulfamoyl group, an acylamino group, a sulfonylamino group, or nitro group; $R^6$ represents hydrogen atom, a $C_{1-4}$ alkyl group, or a $C_{1-4}$ alkylcarbonyl group; n represents 1 or 2; and L represents a linking group selected from a $C_{4-11}$ alkylene group or an alkylene group containing one or more ether groups and having 5–8 atoms constituting a full length of a linking chain.

4. The compound according to claim 1, wherein Y represents a single bond or sulfur atom; $R^5$ represents hydrogen atom, a halogen atom, a $C_{1-4}$ alkyl group, a $C_{1-4}$ alkoxy group, a $C_{1-4}$ alkoxycarbonyl group, a $C_{1-4}$ alkylcarbamoyl group, a $C_{1-4}$ alkylsulfamoyl group, a $C_{1-4}$ alkylcarbonylamino group, a $C_{1-4}$ alkylsulfonylamino group, or nitro group; $R^6$ represents hydrogen atom, a $C_{1-4}$ alkyl group, or a $C_{1-4}$ alkylcarbonyl group; n represents 1 or 2; and L represents a linking group selected from a $C_{4-11}$ alkylene group or an alkylene group containing one or more ether groups and having 5–8 atoms constituting a full length of a linking chain.

5. The compound according to any one of claims 2 to 4, wherein n represents 2, and the two $R^5$ groups are substituted at the 5- and 6-positions of the benzimidazole ring.

6. The compound according to claim 5, wherein $R^5$ represents hydrogen atom, a halogen atom, a $C_{1-4}$ alkyl group, or nitro group, and $R^6$ represents hydrogen atom when Y represents a single bond.

7. The compounds according to claim 5, wherein Y represents sulfur atom when L represents an alkylene group containing one or more ether groups and having 5–8 atoms constituting a full length of a linking chain.

8. The compound according to claim 7, wherein $R^5$ represents hydrogen atom.

9. The compound according to claim 8, wherein Q represents a substituted or unsubstituted 1,3,4-oxadiazole ring.

10. The compound according to claim 8, wherein Q represents a substituted or unsubstituted 1,2,4-oxadiazole ring.

* * * * *